(12) United States Patent
Lionetti et al.

(10) Patent No.: US 12,150,685 B2
(45) Date of Patent: Nov. 26, 2024

(54) VARIABLE ANGLE PLATE TENSIONING DEVICES

(71) Applicant: Stryker European Operations Limited, Carrigtwohill (IE)

(72) Inventors: Leonardo Lionetti, Zurich (CH); Ana Trapero Martin, Cork (IE); Lance N. Terrill, Glounthaune (IE)

(73) Assignee: Stryker European Operations Limited, Carrigtwohill (IE)

( * ) Notice: Subject to any disclaimer, the term of this patent is extended or adjusted under 35 U.S.C. 154(b) by 232 days.

(21) Appl. No.: 17/831,057

(22) Filed: Jun. 2, 2022

(65) Prior Publication Data
US 2023/0389971 A1    Dec. 7, 2023

(51) Int. Cl.
| | | |
|---|---|---|
| *A61B 17/88* | (2006.01) | |
| *A61B 17/17* | (2006.01) | |
| *A61B 17/66* | (2006.01) | |
| *A61B 17/68* | (2006.01) | |
| *A61B 17/72* | (2006.01) | |
| *A61B 17/80* | (2006.01) | |
| *A61B 17/86* | (2006.01) | |

(52) U.S. Cl.
CPC ...... *A61B 17/8863* (2013.01); *A61B 17/1728* (2013.01); *A61B 17/8061* (2013.01); *A61B 17/809* (2013.01); *A61B 17/864* (2013.01); *A61B 17/66* (2013.01); *A61B 2017/681* (2013.01); *A61B 17/7216* (2013.01); *A61B 17/7225* (2013.01); *A61B 17/8004* (2013.01); *A61B 17/8019* (2013.01); *A61B 17/8869* (2013.01)

(58) Field of Classification Search
CPC . A61B 17/8869; A61B 17/1728; A61B 17/66; A61B 17/8019; A61B 17/8023; A61B 17/8061; A61B 17/808; A61B 17/809; A61B 17/80; A61B 17/68; A61B 17/7216; A61B 17/7225; A61B 17/8004; A61B 2017/681
USPC ..... 606/53, 101, 57, 60, 280, 282, 86 R, 87, 606/99, 105, 86 B, 902, 915
See application file for complete search history.

(56) References Cited

U.S. PATENT DOCUMENTS 3,386,437 A * 6/1968 Treace ............... A61B 17/8019
606/104
3,400,711 A * 9/1968 Frick ................. A61B 17/8019
606/105

(Continued)

OTHER PUBLICATIONS

"Basic principles of plating," Surgery Reference, Retrieved form the Internet on May 16, 2022, pp. 1-32. https://surgeryreference.aofoundation.org/orthopedic-trauma/adult-trauma/basic-technique/basic-principles-of-plating.

(Continued)

*Primary Examiner* — Marcela I. Shirsat
(74) *Attorney, Agent, or Firm* — Lerner David LLP

(57) ABSTRACT

An articulated tensioning device includes a first foot and a second foot. One of the feet includes a projection configured to engage a fastener hole of a bone plate and the other of the feet includes a hole therethrough for receiving a fastener. The device also includes a slider translatable relative to the first foot and a bridge link pivotably connected to the slider at a first point pivotably connected to the second foot at a second point. A fulcrum link is pivotably connected to the second foot and a third point on the bridge link that is between the first point and the second point.

20 Claims, 21 Drawing Sheets

(56) References Cited

U.S. PATENT DOCUMENTS

| | | | | |
|---|---|---|---|---|
| 4,102,339 A * | 7/1978 | Weber | ............... | A61B 17/8019 |
| | | | | 606/105 |
| 10,285,742 B1 * | 5/2019 | Patterson | ........... | A61B 17/8019 |
| 2006/0004380 A1 * | 1/2006 | DiDomenico | ..... | A61B 17/8004 |
| | | | | 606/105 |

OTHER PUBLICATIONS

Hansen, M. et al., "Lag screw technique," Surgery Reference, Retrieved from the Internet on May 16, 2022, pp. 1-19. https://surgeryreference.aofoundation.org/orthopedic-trauma/adult-trauma/proximal-tibia/basic-technique/lag-screw-technique.

* cited by examiner

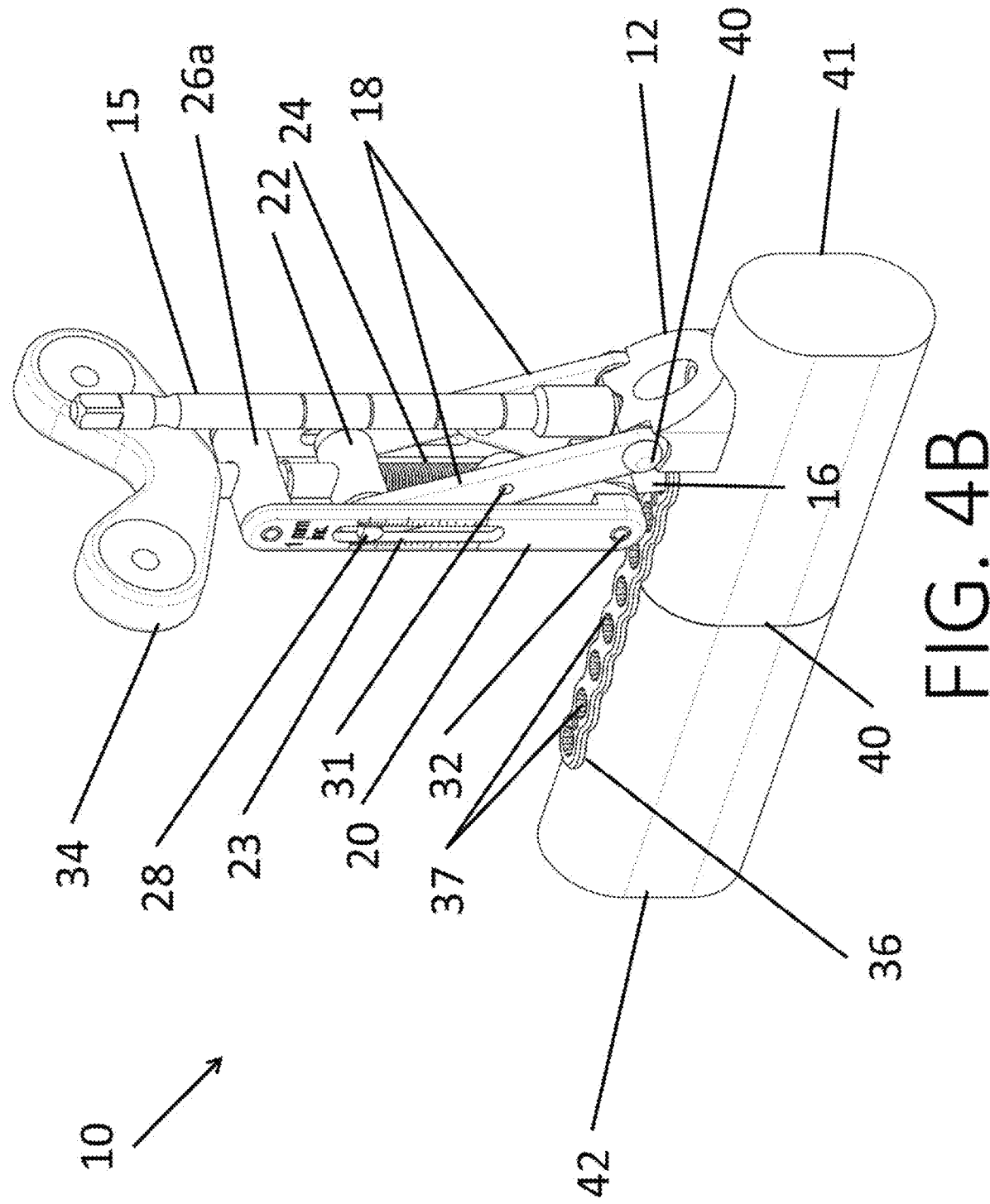

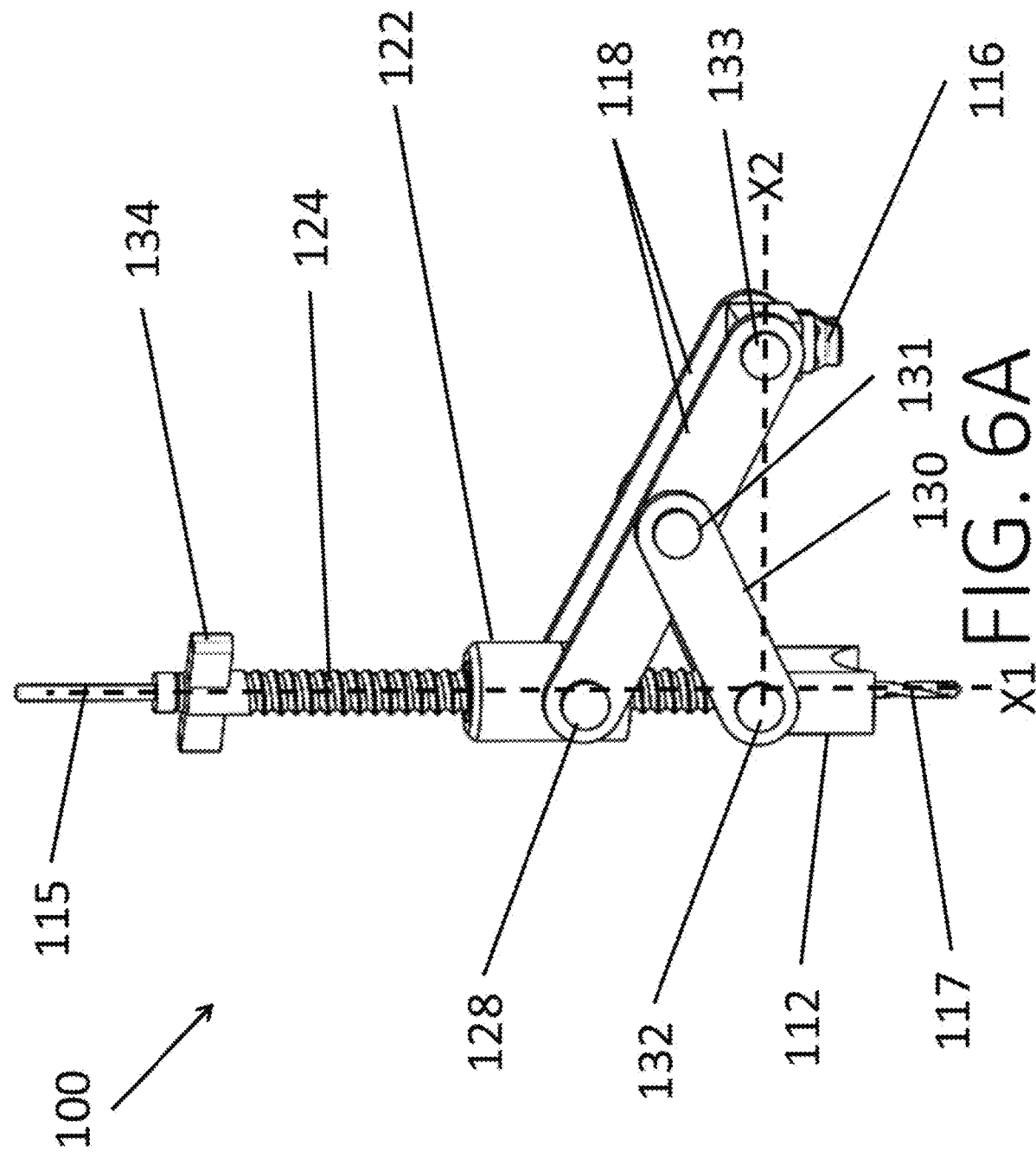

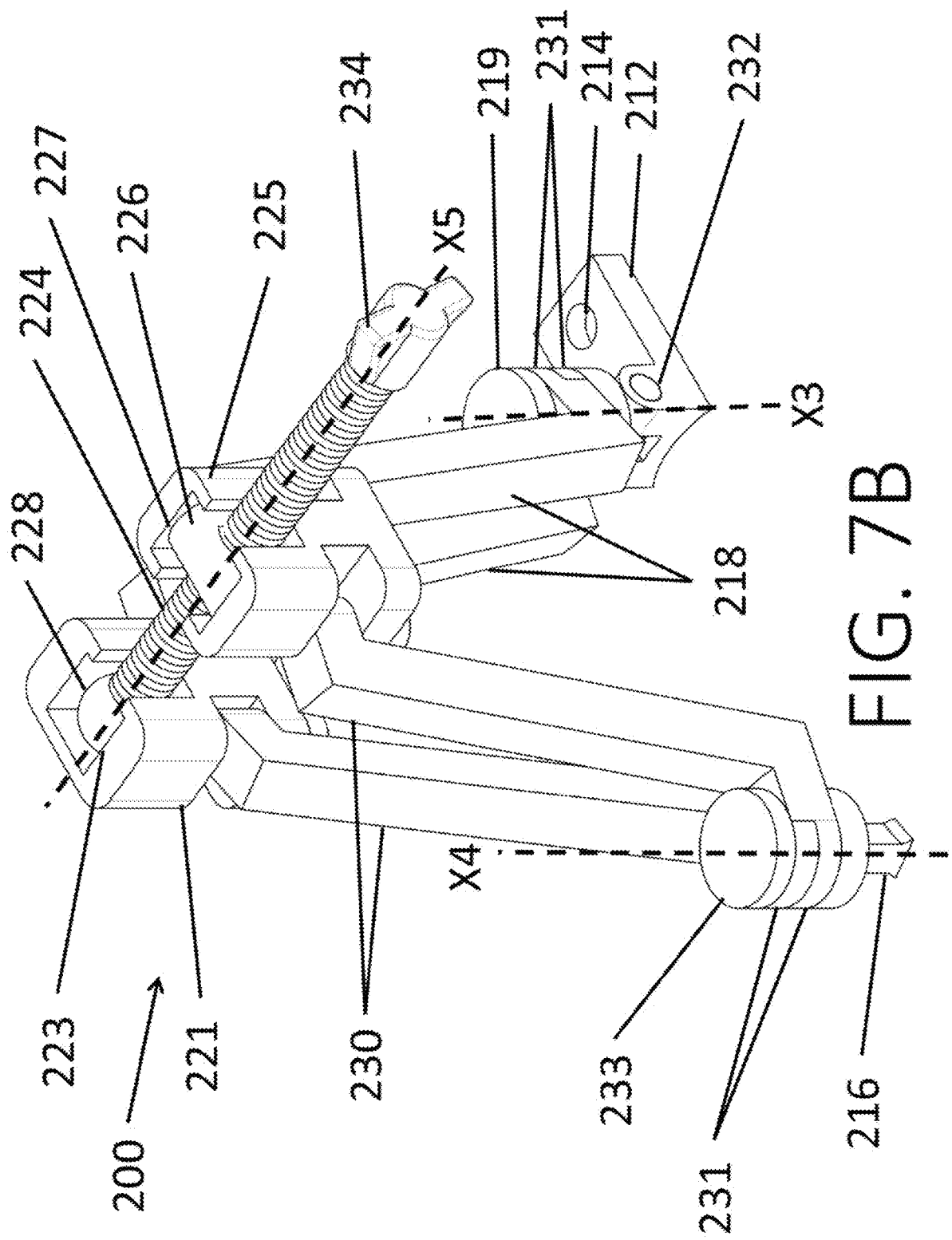

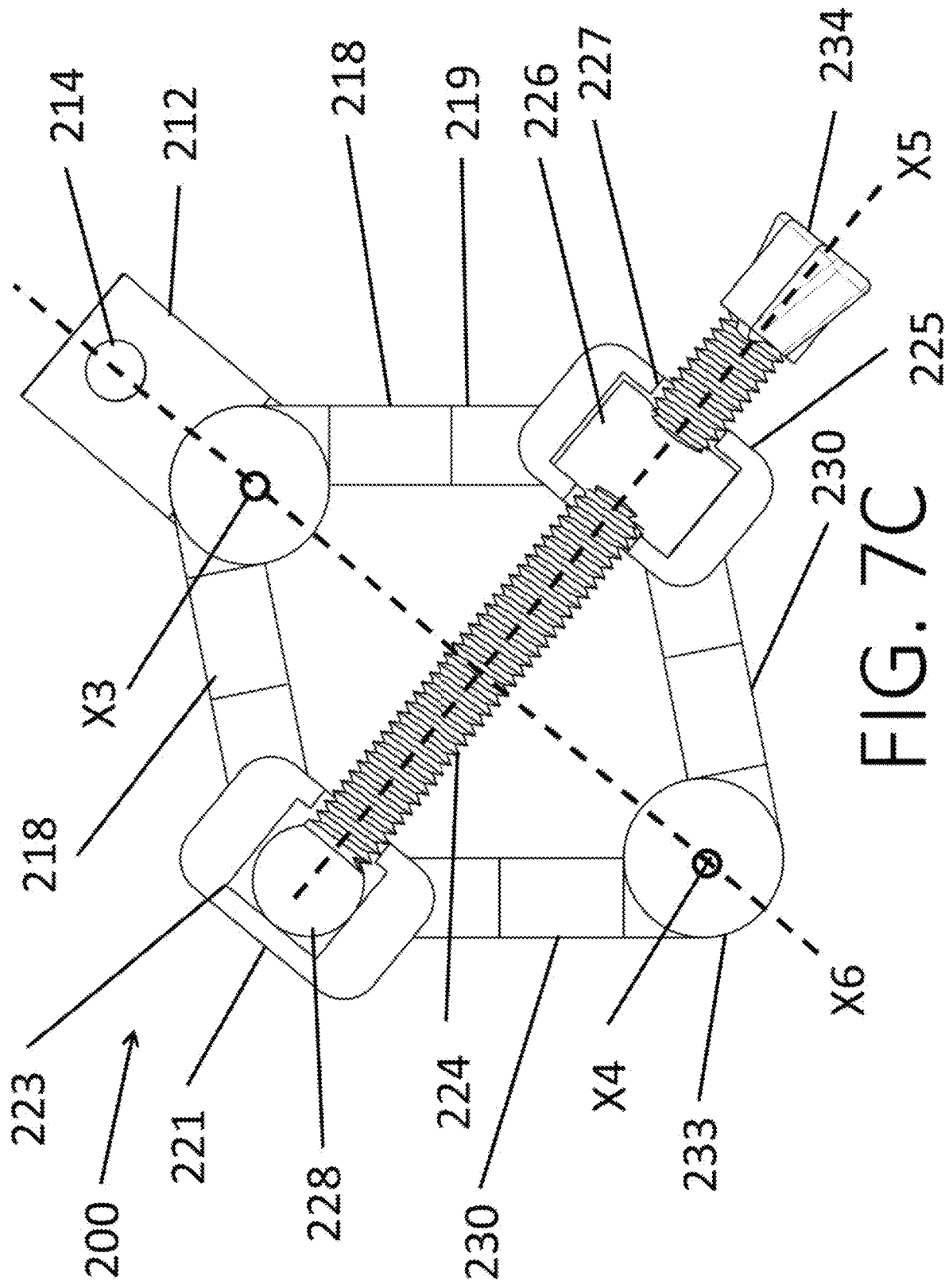

VARIABLE ANGLE PLATE TENSIONING DEVICES

BACKGROUND

Bone fractures and breaks of some varieties can be treated by fastening a plate to the bone across the break or fracture. Some plates for this purpose, known as "variable angle" plates, include fastener holes that are each adapted to be able to receive a fastener and engaged with a head of the fastener at multiple possible angles.

Compression on the fracture or break and proper alignment of the portions of the bone on opposite sides of the fracture or break tends to be conducive to faster and better healing of the bone. Suitable compression and alignment can be difficult to achieve manually, particularly while fasteners are being driven through a bone plate to fasten the plate to the bone for the purpose of maintaining the compression and alignment. Tools for assisting with compressing and aligning bones across fractures could therefore simplify treatment of fractures and breaks and improve patient outcomes.

BRIEF SUMMARY

According to some aspects, a tensioning device may include two feet. One of the feet may include a protrusion for engaging a hole of a bone plate, such as a variable angle plate, and the other of the feet may include a fastener hole or other feature enabling fixation of the foot to the bone. A guide may be non-translatably connected to one of the feet, and the guide may constrain a slider to motion along a guide axis $X1$. The guide may include a threaded shaft, and the slider may be threadedly engaged with the shaft so that rotating the shaft relative to the foot to which the guide is non-translatably connected causes the slider to travel along the guide axis $X1$. The guide may also include a track or tracks in which a stud or studs of the slider are received, and the tracks may cooperate with the shaft to define the guide axis $X1$. The device may include a bridge link connected at a first point to the slider and at a second point to the one of the feet that is translatable relative to the guide. The device may also include a fulcrum link that is pivotably connected to the foot to which the guide is non-translatably connected and to a third point on the bridge link that is between the first point and the second point. The interaction of the bridge link and the fulcrum link causes the feet to move relative to one another along a reduction axis $X2$ that is transverse to the guide axis $X1$ in response to moving the slider along the guide.

According to some other aspects, a tensioning device may include two feet, two collars, and four links. One of the feet may include a protrusion for engaging a hole of a bone plate, such as a variable angle plate, and the other of the feet may include a fastener hole or other feature enabling fixation of the foot to the bone. Each foot may be rotatably connected to two of the links, each collar may be rotatably connected to two of the links, and each link may be rotatably connected to only one of the feet and one of the collars. The axes about which the links may rotate relative to the feet and the collars may all be mutually parallel. Motion of the collars away from each other may therefore bring the feet nearer to each other and vice versa. The device may also include a threaded bolt having a head rotatably received in one of the collars. The bolt may also be threadedly engaged with an object that is non-rotatably and non-translatably connected to, formed in, or received in the other collar. The distance between the feet may therefore be varied by rotating the bolt about an axis that extends through both collars, thereby bringing the collars nearer together or pushing the collars farther apart.

According to another aspect, an articulated tensioning device may comprise a first foot and a second foot. Either the first foot or the second foot includes a projection configured to engage a fastener hole of a bone plate and the other of the first foot and the second foot includes a hole therethrough for receiving a fastener. The device may also comprise a slider translatable relative to the first foot. The device may also comprise a bridge link pivotably connected to the slider at a first point pivotably connected to the second foot at a second point. The device may also comprise a fulcrum link pivotably connected to the second foot and a third point on the bridge link that is between the first point and the second point.

In some arrangements according to any of the foregoing, the device may also comprise a guide that constrains translation of the slider to an axis defined relative to the guide.

In some arrangements according to any of the foregoing, the guide may be nontranslatable relative to the first foot.

In some arrangements according to any of the foregoing, the guide axis may be immovable relative to the first foot.

In some arrangements according to any of the foregoing, the guide may comprise a shaft extending through the slider and along the shaft axis, and along which the slider is translatable.

In some arrangements according to any of the foregoing, the shaft may be externally threaded and the guide is internally threaded.

In some arrangements according to any of the foregoing, the shaft may be cannulated.

In some arrangements according to any of the foregoing, the bridge link may be a first bridge link and comprising a second bridge link pivotably connected to the slider at a fourth point and pivotably connected to the second foot at a fifth point.

In some arrangements according to any of the foregoing, the fulcrum link may be a first fulcrum link and further comprising a second fulcrum link pivotably connected to the first foot and a sixth point on the second fulcrum link that is between the fourth point ant the fifth point.

In some arrangements according to any of the foregoing, the device may comprise a post extending from the second foot, a collar slidable along the post, and an arm pivotably connected to the collar and to a fixed point on the guide.

In some arrangements according to any of the foregoing, the post may be non-rotatable relative to the second foot.

In some arrangements according to any of the foregoing, the arm may be a first arm, and comprising a second arm extending from the collar.

In some arrangements according to any of the foregoing, the guide may comprise a track link that defines an elongate track extending parallel to the guide axis and the slider includes a stud received in the track.

In some arrangement according to any of the foregoing, an articulated tensioning device may comprise a first foot and a second foot. Either the first foot or the second foot may include a projection configured to engage a fastener hole of a bone plate and the other of the first foot and the second foot includes a hole therethrough for receiving a fastener. The device may also comprise a first collar and a second collar. The device may also comprise a first link connected to the first foot, rotatable relative to the first foot about a first axis, connected to the first collar, and rotatable relative to the first collar about a second axis. The device may also comprise a second link connected to the first foot, rotatable relative to the first foot about a third axis, connected to the second collar, and rotatable relative to the second collar about a fourth axis. The device may also comprise a third link connected to the second foot, rotatable relative to the second foot about a fifth axis, connected to the first collar, and rotatable relative to the first collar about a sixth axis. The device may also comprise a fourth link connected to the second foot, rotatable relative to the second foot about a seventh axis, connected to the second collar, and rotatable relative to the second collar about an eighth axis. The first, second, third, fourth, fifth, sixth, seventh, and eighth axes may be parallel to one another and none of the first, third, fifth, or seventh axes are coaxial with any of the second, fourth, sixth, or eighth axes.

In some arrangements according to any of the foregoing, the device may also comprise a threaded shank extending through the first collar and into the second collar.

In some arrangements according to any of the foregoing, the first collar may include an internally threaded portion.

In some arrangements according to any of the foregoing, the device may comprise a nut threaded onto the threaded shank and received in the first collar.

In some arrangements according to any of the foregoing, the device may comprise a bolt that includes the threaded shank and a head, the head being rotatably received in a socket defined by the second collar.

In some arrangements according to any of the foregoing, the head may be at least partially spherical.

In some arrangements according to any of the foregoing, the shank may be rotatable about a ninth axis perpendicular to the first, second, third, fourth, fifth, sixth, seventh, and eighth axes.

In some arrangements according to any of the foregoing, the first axis may be coaxial with the third axis and the fifth axis is coaxial with the seventh axis.

In another aspect, a method of reducing two bone portions may comprise anchoring a foot of an articulated tensioning device to a first portion among the bone portions. The method may also comprise hooking a protrusion of the articulated tensioning device to a bone plate fastened to a second portion among the bone portions. The method may also comprise moving a slider of the articulated tensioning device along a guide away from the bone portions to bring the foot and the protrusion together thereby moving the first and second bone portions with respect to each other. The guide may be non-translatably connected to either the foot or the protrusion and a bridge link is connected at a first point to the slider and at a second point to the other of the foot and the protrusion.

In some arrangements according to any of the foregoing, the device may comprise a fulcrum link rotatably connected to a third point on the bridge link between the first point and the second point and to the guide.

In some arrangements according to any of the foregoing, the slider may comprise rotating a threaded shaft with which the collar is threadedly engaged.

In some arrangements according to any of the foregoing, the method may comprise rotating one of the bone portions relative to the other of the bone portions by guiding a collar along a post that extends from the foot after the anchoring and hooking steps. The guide may be non-translatably connected to the protrusion, and the post extends from the foot, the post extends through the collar, and a rigid link is connected to the collar and the guide.

In some arrangements according to any of the foregoing, the rotating step may be performed before the step of moving a slider.

In another aspect, a reduction assembly for reducing bones or bone portions may comprise a screw having a shank. The shank may include a distal portion that is externally threaded with threads. The shank may also include an anchoring portion proximal of the distal portion. The anchoring portion may include radially extending blades configured to impede withdrawal in a proximal direction along a proximal-distal axis of the reduction screw from any bone in which the anchoring portion may be embedded. The shank may also include a proximal portion that is proximal of the anchoring portion and externally threaded. The assembly may also include an internally threaded nut threaded onto the proximal portion.

In another aspect, a method of reducing a gap between two bone portions, the method may comprise driving the screw through a first bone portion and into a second bone portion until the anchoring portion is embedded in the second bone portion. The method may also comprise threadedly advancing a nut distally along the proximal portion against a surface of the first bone portion.

In another aspect, a reduction assembly may comprise a cross guide including a first slot and a second slot transverse to the first slot. The assembly may also comprise a spool disposed in the first slot and configured to travel along the first slot. The reduction assembly may also comprise a slider disposed in the second slot and configured to travel along the second slot. The reduction assembly may also comprise a wire connected to the spool and the slider.

In some arrangements according to any of the foregoing, the spool may include an axle slidable along the first slot and a drum rotatable about the axle, and the wire is connected to the spool so as to be windable about the drum.

In some arrangements according to any of the foregoing, the slider and the spool may each include a hole for receiving a bone screw therethrough.

In some arrangements according to any of the foregoing, the first slot may extend perpendicular to the second slot.

In some arrangements according to any of the foregoing, the first slot may be centered along a length of the second slot so that the first and second slots are arranged in a T-shape.

In another aspect, a reduction assembly may comprise a link having a first fastener hole extending therethrough. The assembly may also comprise a bolt pivotably connected to the link and including a threaded shank. The assembly may also comprise a frame having a second fastener hole extending therethrough, a first aperture through which the shank is disposed, and a second aperture. The reduction assembly may also comprise a gear nut and threaded onto a portion of the shank on an opposite side of the first aperture from the link. The reduction assembly may also comprise a driver including a shaft disposed through the second aperture and ending in a gear wheel engaged with the gear nut.

In some arrangements according to any of the foregoing, the frame may include a third fastener hole extending therethrough.

In some arrangements according to any of the foregoing, the external teeth of the gear nut and the gear wheel may be bevel gear teeth and the shank extends transverse to the shaft.

In some arrangements according to any of the foregoing, the bolt may be pivotably connected to the link by a ball and socket joint.

In another aspect, a reduction assembly may comprise an elongate plate including a series of teeth defining a rack. The assembly may also comprise a frame through which the plate extends. The assembly may also comprise a pinion engaged with the rack and rotatably, but non-translatably, connected to the block. The assembly may also comprise a lever connected to the frame to be rotatable relative to the frame along a rotation axis about which the pinion is rotatable relative to the block. The assembly may also comprise a pawl pivotably connected to the lever and engageable with teeth of the pinion to transfer torque from the lever to the pinion in a driving direction about the rotation axis.

In some arrangements according to any of the foregoing, the pawl may be a first pawl. The assembly may comprise a second pawl pivotably connected to the block and engageable with the teeth of the pinion to prevent the pinion from rotating opposite the driving direction.

BRIEF DESCRIPTION OF THE DRAWINGS

FIG. 4B is an oblique perspective view of the assembly and bone portions of FIG. 4A in which the articulated tensioning device is in the second position.

FIG. 6A is an oblique perspective view of an articulated tensioning device according to another aspect of the present disclosure.

FIG. 7B is an oblique perspective view of the articulated tensioning device of FIG. 7a in a fully assembled state.

FIG. 7C is a top plan view of the articulated tensioning device of FIG. 7A.

DETAILED DESCRIPTION

As used herein, the term "proximal," when used in connection with a surgical tool or device, or components of a device, refers to the end of the device closer to the user of the device when the device is being used as intended. On the other hand, the term "distal," when used in connection with a surgical tool or device, or components of a device, refers to the end of the device farther away from the user when the device is being used as intended. As used herein, the terms "substantially," "generally," "approximately," and "about" are intended to mean that slight deviations from absolute are included within the scope of the term so modified, such as deviations of up to 10% greater or lesser than absolute. All vertical directional terms, such as "up," "down," "above," "below," "vertical," or "height" used in the following description refer only to the orientation of features as depicted in the figure being described. Such directional terms are not intended to suggest that any features of the devices described herein must exist in any particular orientation when constructed.

Figure 1A:
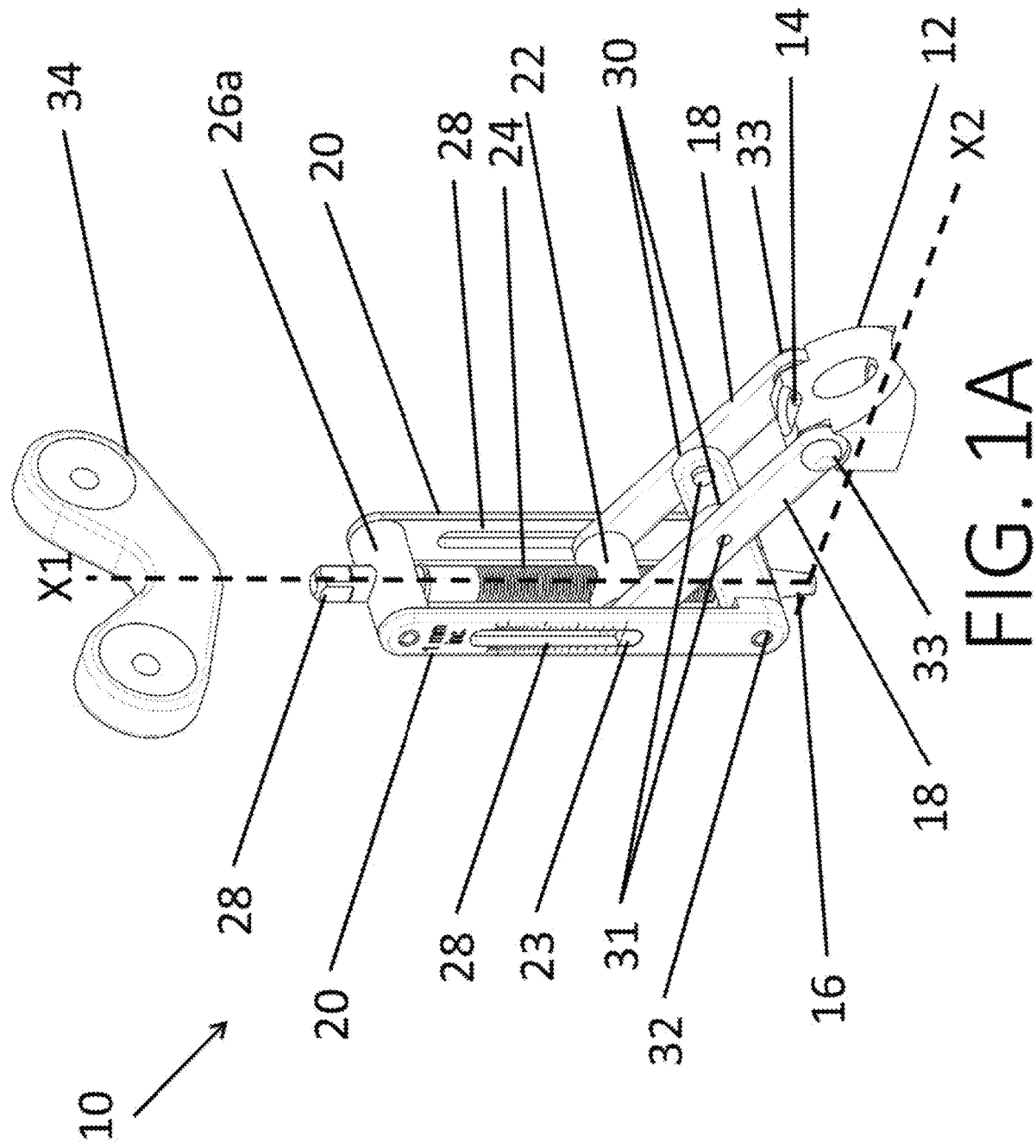
FIG. 1A is an oblique perspective view of an articulated tensioning device.

FIG. 1A illustrates an articulated tensioning device 10. Device 10 includes two feet in the form of a block 12 and a protrusion 16. Block 12 includes an aperture 14 through which a fastener may be disposed to fasten block 12 to bone, thereby anchoring device 10 to the bone. Protrusion 16 is shaped to engage a fastener hole in a bone plate, such as, for example, a variable angle fastener hole. Protrusion 16 of the illustrated example is frustoconical in shape, but in other examples may be, for example, cylindrical, hook shaped, or any other shape capable of engaging a fastener hole of a bone plate to drag the bone plate in a direction normal to the central axis of the fastener hole. In some examples, a lower end of protrusion 16 has a lip extending outwardly therefrom to facilitate engagement with the bone plate.

Device 10 also includes a slider 22, which is translatable relative to protrusion 16, but constrained to translation along a guide axis X1 non-translatably defined relative to protrusion 16, a pair of bridge links 18, and a pair of fulcrum links 30. Slider 22 includes studs 23 extending laterally in opposite directions. Each bridge link 18 is connected at a respective first point thereon to slider 22 to be rotatable about a respective stud 23. Each bridge link 18 is also rotatably connected at a respective second point 33 thereon to block 12. Each fulcrum link 30 is pivotably connected to protrusion 16 and to a respective bridge link 18 at a respective third point 31 that is between that bridge's 18 first point and second point 33. Thus, travel of slider 22 away from protrusion 16 along the guide axis X1 will cause block 12 to travel toward protrusion 16 and travel of slider 22 toward protrusion 16 along the guide axis X1 will cause block 12 to travel away from protrusion 16. Because slider's 22 travel is constrained to the guide axis X1 and fulcrum links 30 ensure that third points 31 on bridge links 18 will always be at a constant distance from fulcrum hinge 32 that rotatably connects fulcrum links 30 to protrusion 16, movement of slider 22 along the guide axis X1 will cause block 12 and protrusion 16 to move toward or away from one another along a reduction axis X2. The reduction axis X2 is transverse to the guide axis X1 and the position of the reduction axis X2 is a result of the position of the guide axis X1 and the lengths of fulcrum links 40 and bridge links 18.

The travel of block 12 strictly along a reduction axis X2 as described herein and shown in the illustrated arrangement results from the distance between stud 28 and third point 31 equaling the distance between fulcrum hinge 32 and third point 31 and the distance between second point 33 and third point 31. In other examples, the path of block 12 relative to protrusion 16 can be made non-linear by changing the proportions of fulcrum links 30 to bridge links 18 and by changing the location of third points 31 along bridge links 18.

The guide axis X1 is defined by a guide that is non-translatably connected to protrusion 16. In the illustrated example, the guide includes a shaft 24 that extends along the guide axis X1 and a pair of guide links 20 positioned on either side of shaft 24. Shaft 24 extends through slider 22 so that slider 22 can travel along shaft 24. Guide links 20 each define a linear track 23 extending parallel to the guide axis X1 and shaft 24. Studs 23 on either side of slider 22 extend into tracks 28, so shaft 24 and guide links 20 cooperate to constrain slider 22 to the guide axis X1. Shaft 24 is externally threaded and slider 22 is threadedly engaged with shaft 24 while slider is prevented from rotating by the engagement of studs 23 by bridge links 18 and tracks 28, so rotating shaft 24 about the guide axis X1 will cause slider 22 to advance toward or away from protrusion 16 along the guide axis X1. In other examples, shaft 24 may lack threading, and the slider 22 may be advanced along shaft 24 in other ways (e.g., rack and pinion constructs). In further examples, the guide may lack guide links 20 so that the guide axis X1 is defined by shaft 24, or the guide may lack shaft 24 so that the guide axis X1 is defined by tracks 28.

Shaft 24 is constrained to be rotatable about the guide axis X1 but otherwise immobile relative to guide links 20 by cross bars 26a, 26b having apertures aligned on the guide axis X1 and into which shaft 24 extends. Only a proximal cross bar 26a is visible in FIG. 1A, but a distal cross bar 26b can be observed in FIGS. 5A and 5B. Cross bars 26a, 26b are connected to both guide links 20 and therefore serve to hold the guide together in addition to constraining shaft 24 relative to guide links 20.

Figure 1B:
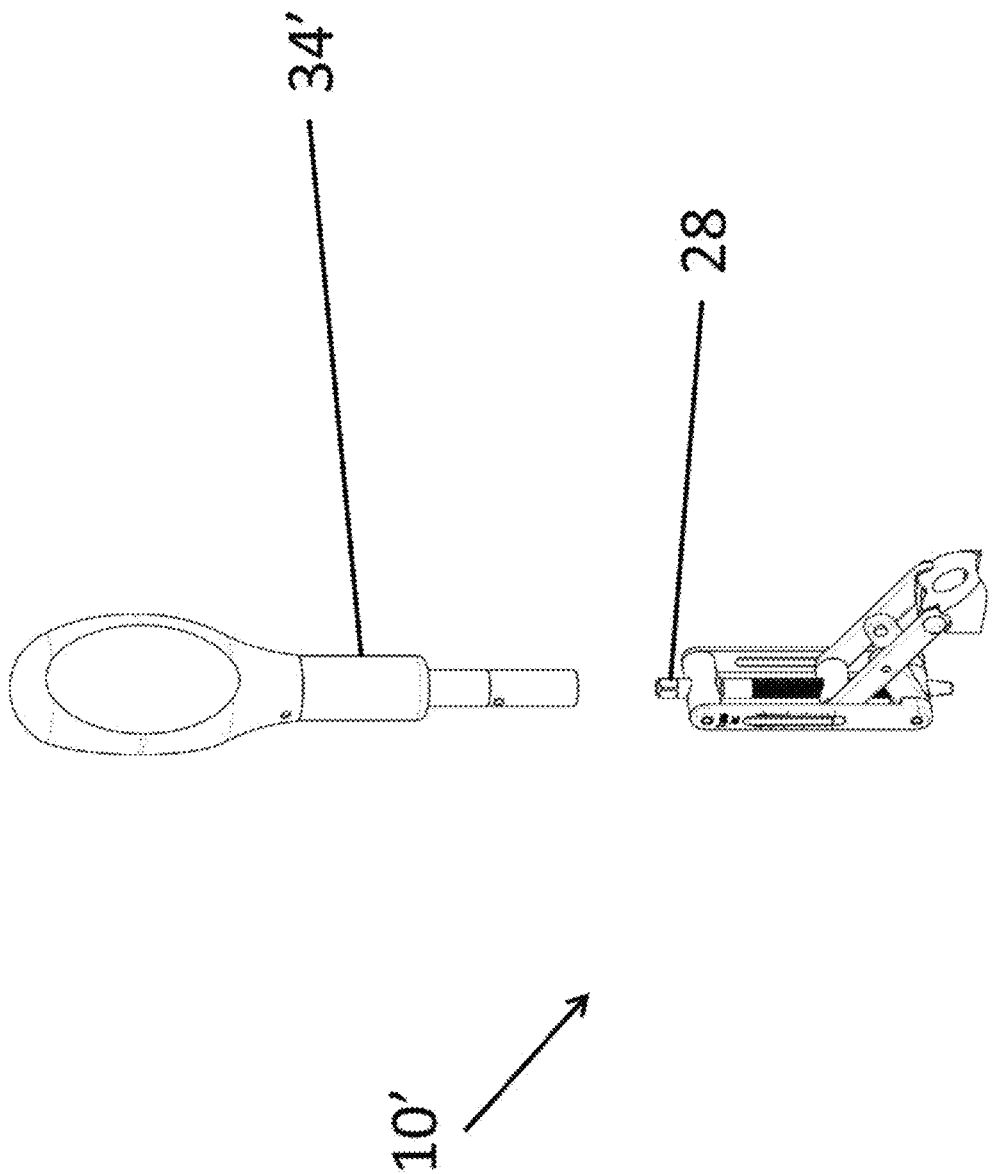
FIG. 1B is an oblique perspective view of the articulated tensioning device of FIG. 1A with a different knob.

A drive head 28 defines a proximal end of shaft 24. Drive head 28 is non-cylindrical, and can therefore be engaged by a driving tool chuck or by correspondingly shaped features of attachments, such as a matching recess (not illustrated) in wing handle 34. Wing handle 34 includes two radially extending flanges to give a user leverage for turning shaft 34 by hand. In another example, a device 10' (see FIG. 1B) is the same as device 10 in all respects except that device 10' includes a barrel handle 34' that is similarly engageable to drive head 28. In other examples, drive head 28 could be any other shape or, instead of drive head 28, a handle may be integrally formed at the proximal end of shaft 24.

Figure 2A:
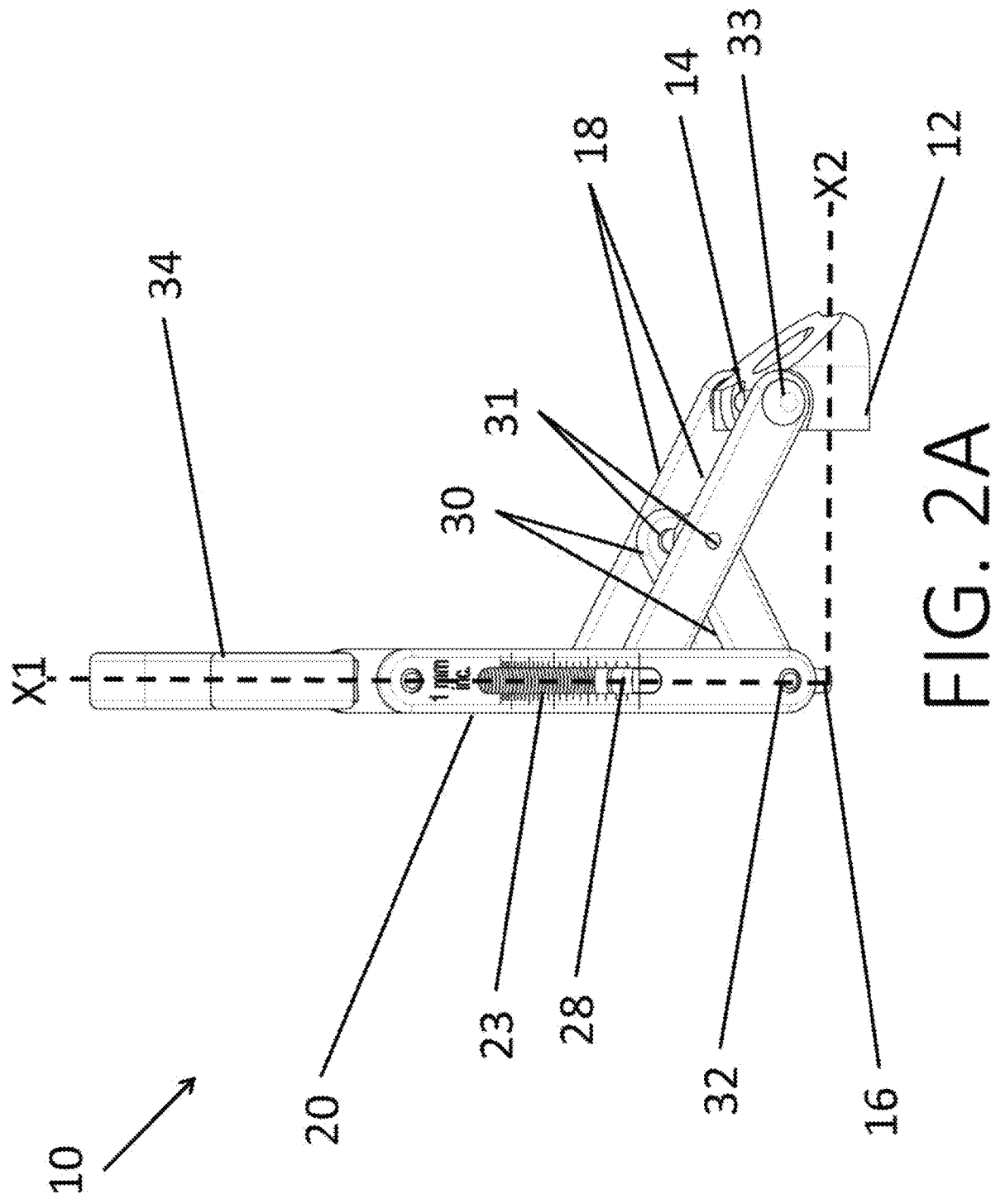
FIG. 2A is a side perspective view of the articulated tensioning device of FIG. 1A in a first position.
Figure 2B:
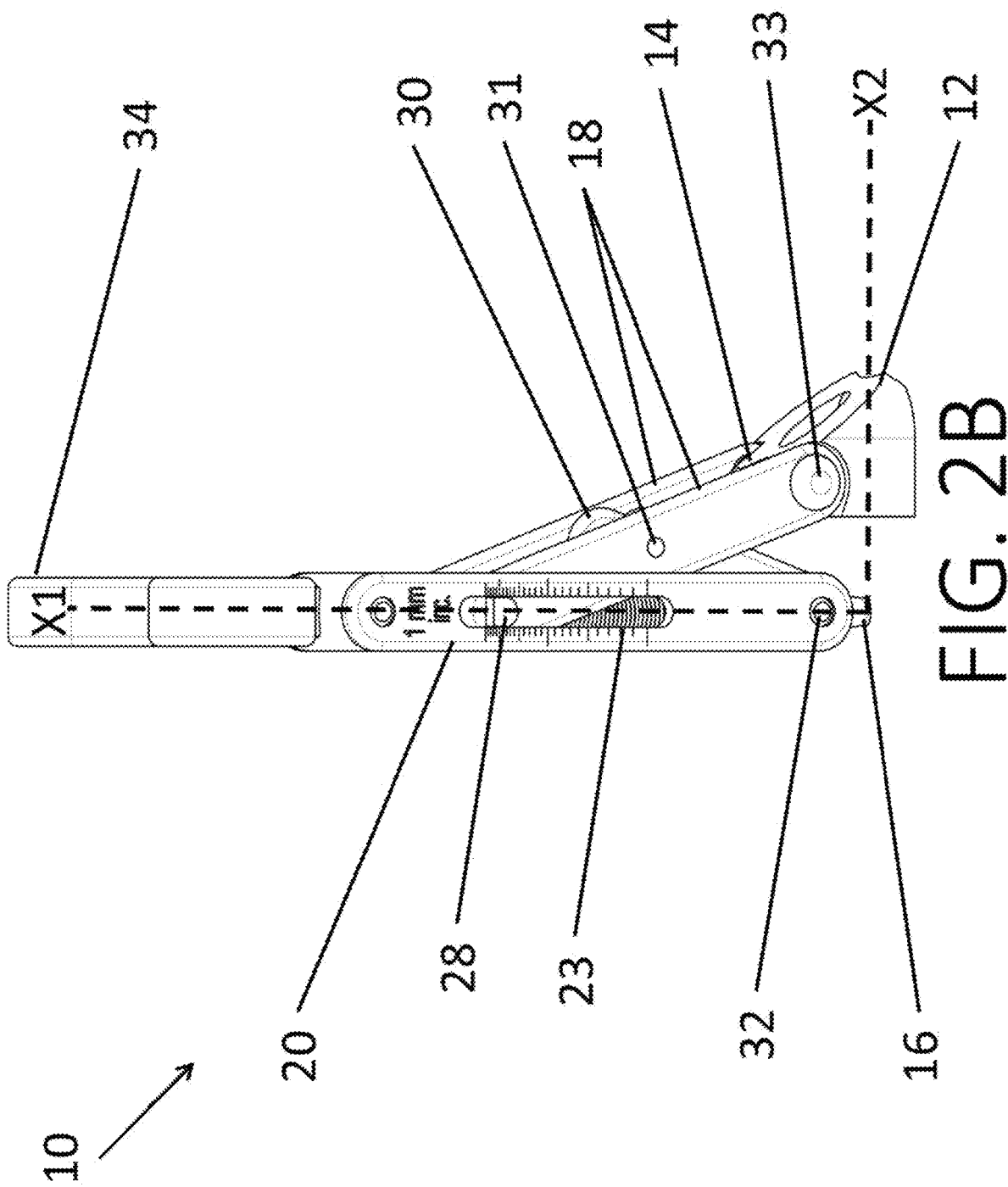
FIG. 2B is a side perspective view of the articulated tensioning device of FIG. 1A in a second position.

Turning to FIGS. 2A and 2B, the distance between block 12 and protrusion 16 is inversely related to the distance between slider 22 and protrusion 16. Turning shaft 24 to advance slider 22 away from protrusion 16, as shown in the transition from FIG. 2A to FIG. 2B, therefore draws block 12 from a position relatively far from protrusion 16 as shown in FIG. 2A to a position relatively near to protrusion 16 as shown in FIG. 2B. Turning shaft 24 in an opposite direction to send slider 22 nearer to protrusion 16 would instead push block 12 away from protrusion 16.

Figure 3:
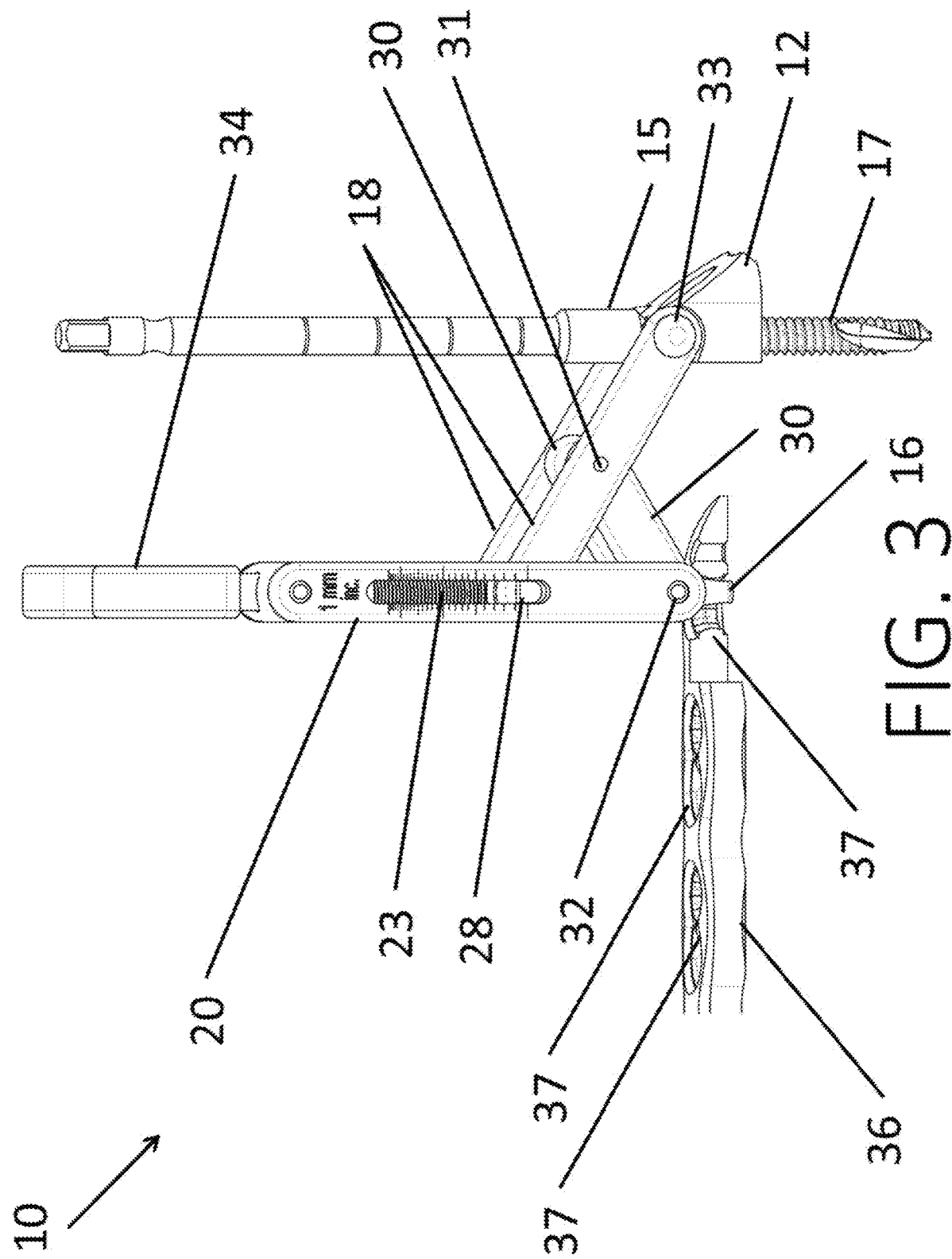
FIG. 3 is a side perspective view of an assembly including the articulated tensioning device of FIG. 1A, a screw, a post, and a bone plate in partial cross-section.

As shown in FIG. 3, device 10 can be used in cooperation with a bone plate 36 and a fastener 17. Fastener 17 in the illustrated example is a self-tapping bone screw, but in other examples fastener 17 could be a non-self-tapping screw or another type of fastener altogether (e.g., an unthreaded peg or the like). Bone plate 36 includes fastener holes 37 that can receive protrusion 16. Protrusion 16 is shaped to engage with the edge surfaces of fastener holes 37 so that protrusion 16 can be used to drag plate 36 in a direction transverse to the direction that fastener holes 37 extend through plate 36. Specifically, in the example shown, plate 36 is planar, or at least a portion of plate 36 is at least approximately planar, and protrusion 16 can be used to drag plate 36 along a plane on which plate 36 lies or the portion of plate 36 approximates. Driving slider 22 along the guide of device 10 can therefore drive fastener 17 and plate 16 together or apart when device 10, plate 36, and fastener 17 are situated generally as shown.

Also shown in FIG. 3 is an elongate post 15 coupled to a proximal end of fastener 17 and extending from block 12. Post 15 is coupled to fastener 17 so as to be non-rotatable relative to block 12 except for about fastener's 17 central axis, meaning post 15 can be manipulated to rotate block 12 about an axis on which both second points 33 lie. Post 15 may be, for example, a driving tool for fastener 17 or a stem integrally formed with fastener 17 but constructed to break away from fastener 17 upon application of a certain amount of torque or tension.

Figure 4A:
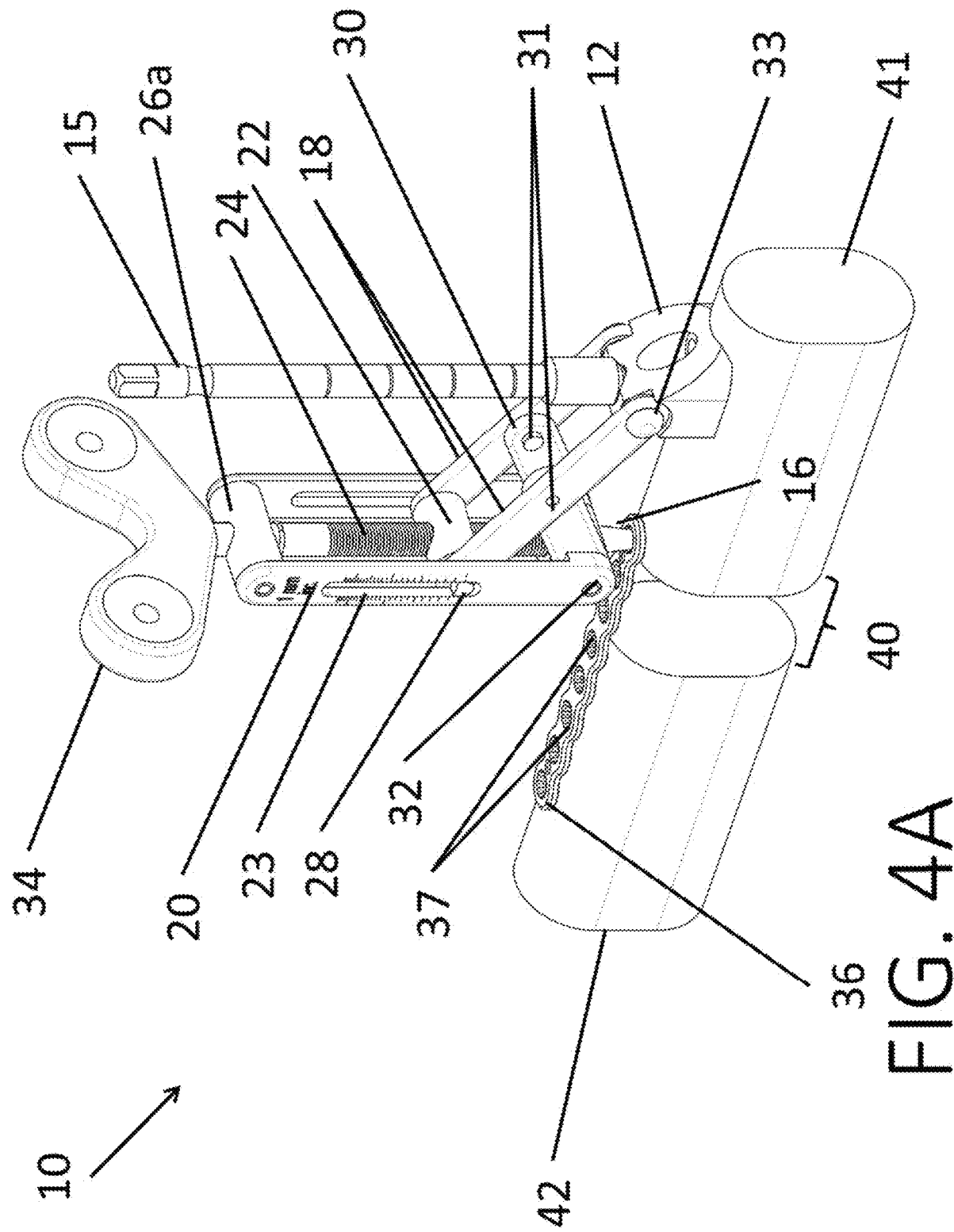
FIG. 4A is an oblique perspective view of the assembly of FIG. 3 in which the articulated tensioning device and bone plate are fastened to respective bone portions and the articulated tensioning device is in the first position.

As shown in FIGS. 4A and 4B, the above described ability to drive slider 22 to draw block 12 and protrusion 16 together and the interaction thereof with plate 36 and fastener 17 can be used to reduce a gap 40 between a first bone portion 41 and a second bone portion 42. Gap 40 may be, for example, a break or fracture while first bone portion 41 and second bone portion 42 are portions of what was previously a single, monolithic bone. However, in other examples, bone portions 41, 42 may be portions of different bones altogether that may be associated with each other at a joint.

Plate 36 is fastened to second bone portion 42 and fastener 17, which is not visible in FIGS. 4A and 4B, fastens block 12 to first bone portion 41. Rotating shaft 24 to draw slider 22 away from protrusion 16 therefore draws first bone portion 41 and second bone portion 42 together and reduces gap 40. Bone plate 36 and device 10 may be positioned so that bone plate 36 extends at least partially across gap 40 before gap 40 is reduced as shown in FIG. 4A and so that plate 36 extends to have at least one fastener hole 37 is positioned over first bone portion 41 after gap 40 is reduced as shown in FIG. 4B. In further examples, plate 36 and device 10 may be positioned so that at least two fastener holes 37 are positioned over first bone portion 41 after gap 40 is reduced, with at least one of those at least two fastener holes 37 being unoccupied by protrusion 16. Device 10 may therefore be used to reduce gap 40 and hold bone portions 41, 42 together while a fastener is driven through the fastener hole 37 positioned over first bone portion 41 to fasten bone plate 36 to first bone portion 41. After bone plate 36 is fastened to first bone portion 41 in this manner, bone plate 36 is fastened to bone portions 41, 42 and thereby joins bone portions 41, 42 together.

Torque may be applied to shaft 24 in an amount exceeding the torque necessary to hold bone portions 41, 42 together while bone plate 36 is being fastened to first bone portion 41. Applying this excess torque will create pressure across gap 40, and such pressure will be preserved by bone plate 36 after bone plate 36 is fastened to both bone portions 41, 42. Device 10 can therefore be used in combination with bone plate 40 to connect bone portions 41, 42 in such a way that bone plate 40 maintains pressure across gap 40 after device 10 is removed from first bone portion 41. Though not illustrated, a gear system may be integrated with or applied to device 10 to increase and maintain torque on shaft 24 and thereby contribute to the loading of bone portions 41, 42 across gap 40.

Figure 5A:
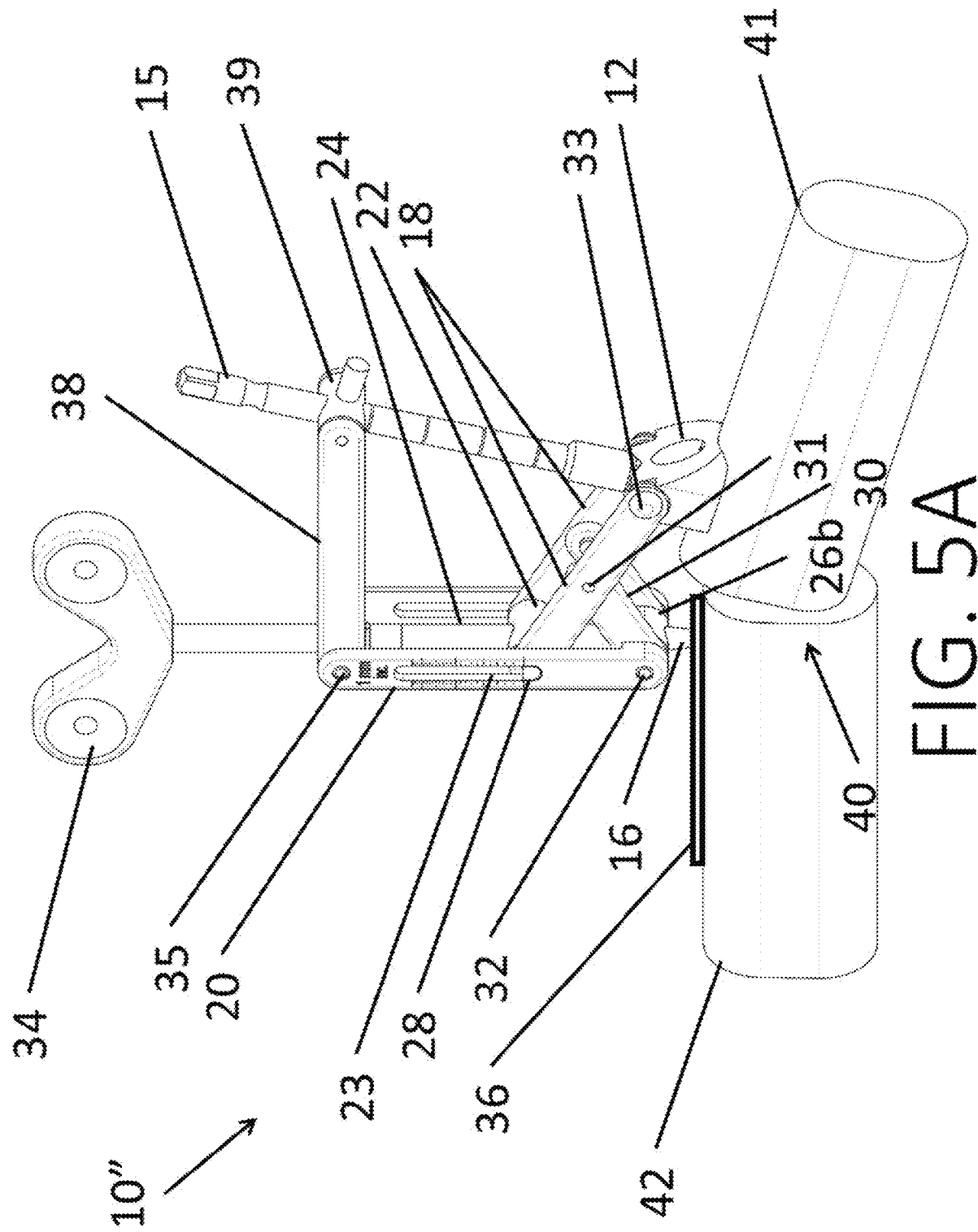
FIG. 5A is an oblique perspective view of the assembly of FIG. 4A in which the articulated tensioning device includes an aligning arm and the bone portions are misaligned.
Figure 5B:
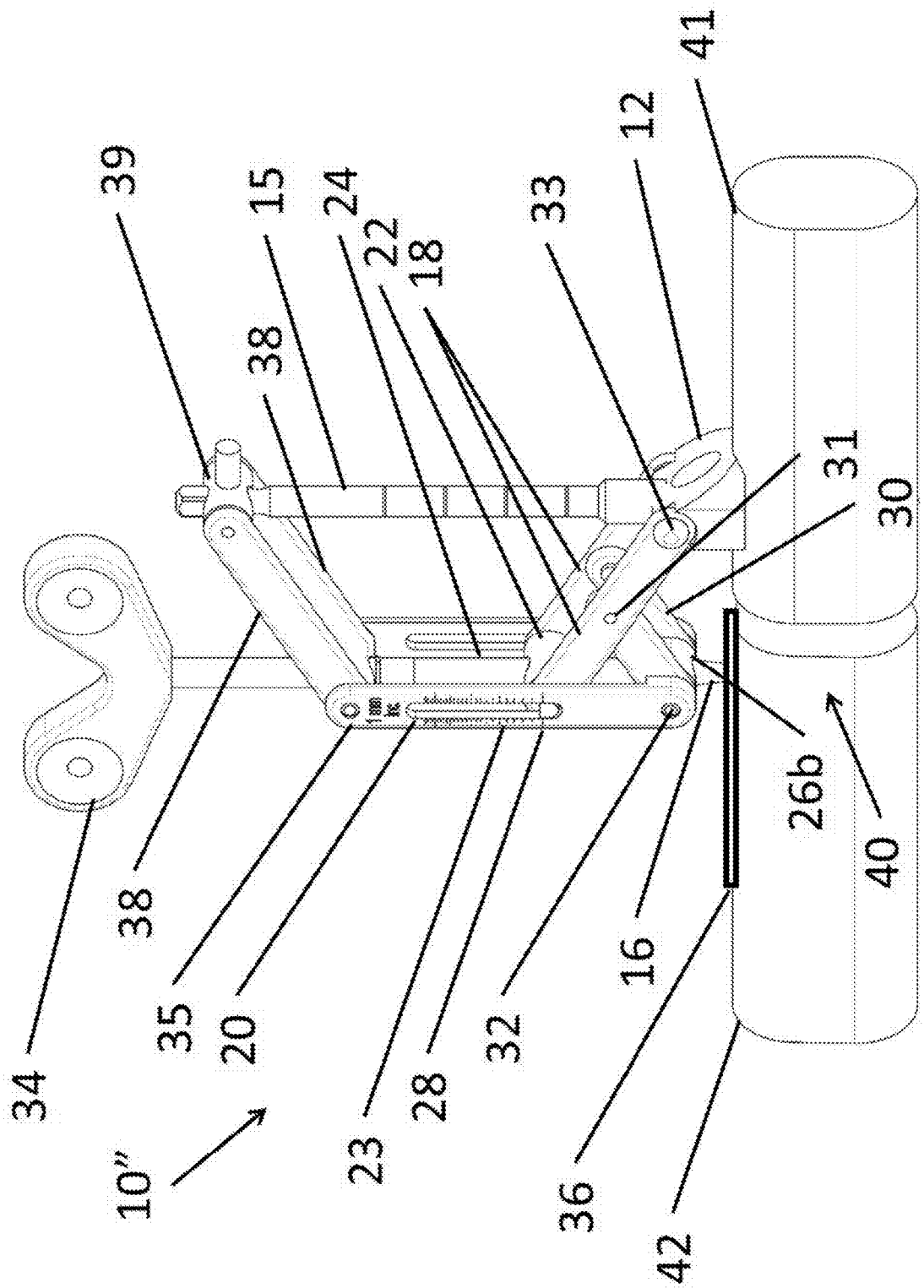
FIG. 5B is an oblique perspective view of the assembly of FIG. 4B in which the bone portions are aligned.

As shown in FIGS. 5A and 5B, device 10 can be provided with an arm or arm links 38 for cooperating with post 15 to manipulate an angle of first bone portion 41 relative to second bone portion 42. Arm links 35 are connected to guide links 20 at an arm hinge 35. A collar 39 is rotatably connected to both arm links 38 at a location spaced from arm hinge 35 and includes an aperture through which post 15 extends. Because arm links 38 are of fixed length, guiding collar 39 up or down post 15 while block 12 is fastened to second bone portion 42 and protrusion 16 is engaged to bone plate 36 with sufficient security can cause post 15, block 12, and first bone portion 41 to rotate about an axis that intersects both second points 33 relative to second bone portion 42. Thus, where bone portions 41, 42 are misaligned as shown in FIG. 5A, arm links 38 and collar 39 can be used in cooperation with post 15 to align bone portions 41, 42 as shown in FIG. 5B before gap 42 is reduced. Protrusion 16 may optionally include a lip, ridge, or hook for engaging bone plate 36, such as by slipping between bone plate 36 and second bone portion 42, to maintain the position of protrusion 16 relative to bone plate 36 as arm links 38 are used to move bone portions 41, 42 relative to one another.

Due to the symmetrical nature of device 10, any one or any combination of the pairs of links described above and illustrated in FIGS. 1A-5B could be, in other examples, a single link on either side of device 10 or a monolithic combination of both of the illustrated links. For example, in other arrangements of device 10, bridge links 18 could be connected to each other near a mutual midpoint to form a monolithic bridge, fulcrum links 30 could be connected to each other near a mutual midpoint to form a monolithic fulcrum, and so on.

Figure 6B:
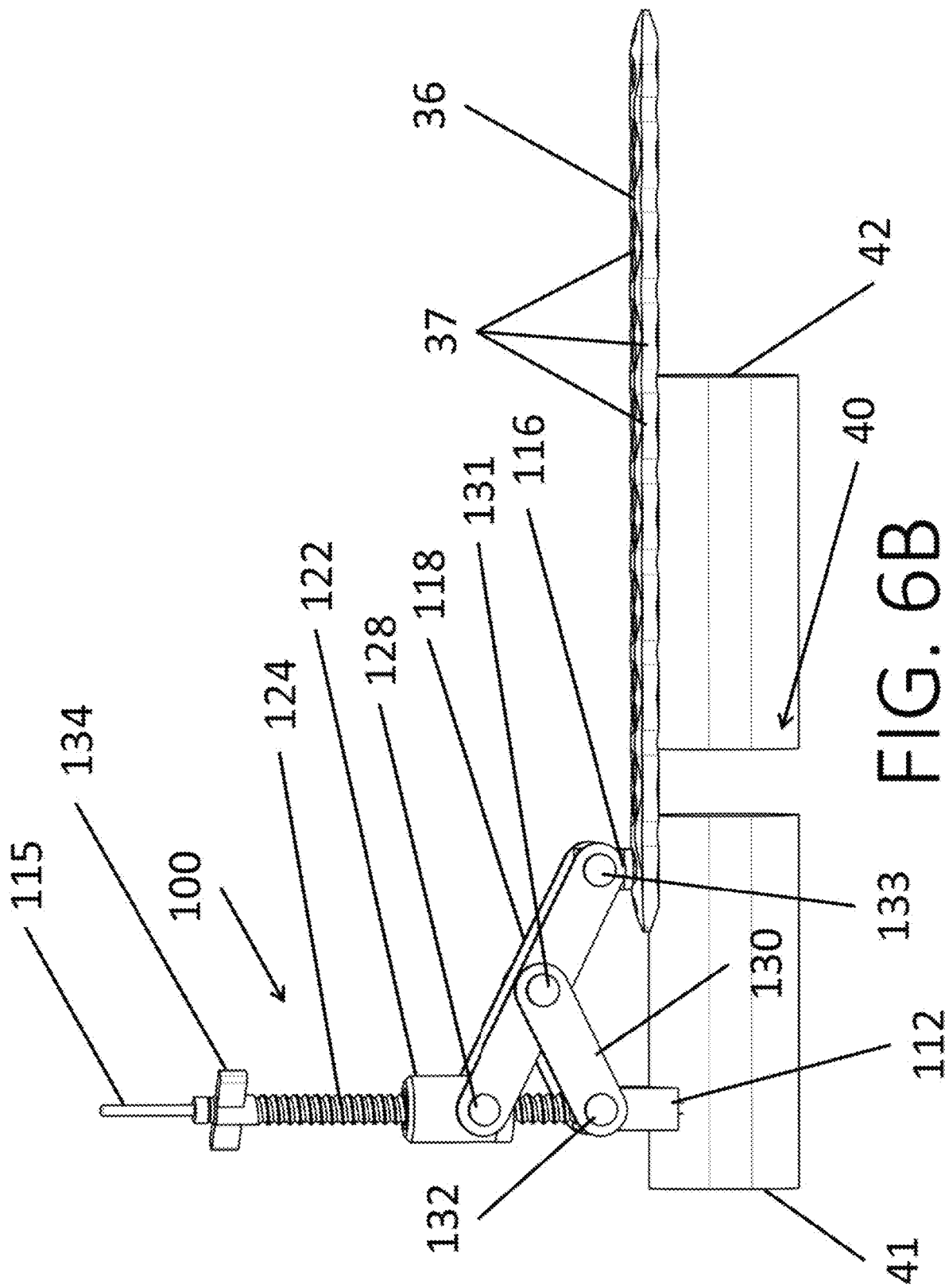
FIG. 6B is a side perspective view of an assembly including the articulated tensioning device of FIG. 6A and bone plate engaged with one another and fastened to respective bone portions.

FIGS. 6A and 6B illustrate a device 100 according to another arrangement. Device 100 is similar to device 10 except for differences specifically described herein or shown in the figures, with like numbered elements denoting like features. That is, bridge links 118 are alike to bridge links 18, fulcrum links 130 are alike to fulcrum links 30, and so on.

Device 100 differs from device 10 in that fulcrum hinge 132 pivotably connects fulcrum links 130 to block 112 instead of protrusion 116. Similarly, protrusion 116 is connected to bridge links 118 to be rotatable about third points 133 of bridge links 118. Shaft 124 extends along and defines a guide axis X1 immovably relative to block 112, so rotating shaft 124 relative to block 112 drives slider 122 toward or away from block 112. Fulcrum links 130 are each rotatably connected to a respective bridge link 118 at a respective third point 131 between that bridge link's 118 first point, corresponding to the point about which that respective bridge link 118 is rotatable about stud 128, and second point 133. Rotating shaft 124 about the guide axis X1 relative to block 112 therefore drives block 112 and protrusion 116 either nearer together or farther apart. A handle 134 is integrally formed with shaft 124 near a proximal end of shaft 124.

Shaft 124 is cannulated, so a wire 115 can extend through shaft 124 and a fastener hole, not visible in FIGS. 6A and 6B, of block 112. Wire 115 can therefore be driven through shaft 124 and block 112 to temporarily fix device 100 to bone, such as first bone 141. Wire 115 may optionally include a drill end 117 to facilitate driving wire 115 into bone. In other arrangements, shaft 124 and block 112 may be cannulated with openings wide enough to receive a fastener and a driver such as fastener 17 and post 15. With device 100 fastened to first bone portion 41 and protrusion 116 received in a fastener hole 37 of a bone plate 36 as shown in FIG. 6A, device 100 may be used to reduce gap 40 and facilitate fastening of bone plate 36 in the same manner as described above with regard to FIGS. 4A and 4B.

In various arrangements other than those illustrated, the differences between device 10 and device 100 could be implemented individually or in any combination. For example, a device could be made exactly alike to device 10 except that the shaft is cannulated to receive a wire, the block is located at the distal end of the shaft, and the protrusion is pivotably connected to the second points of the bridge links.

Figure 7A:
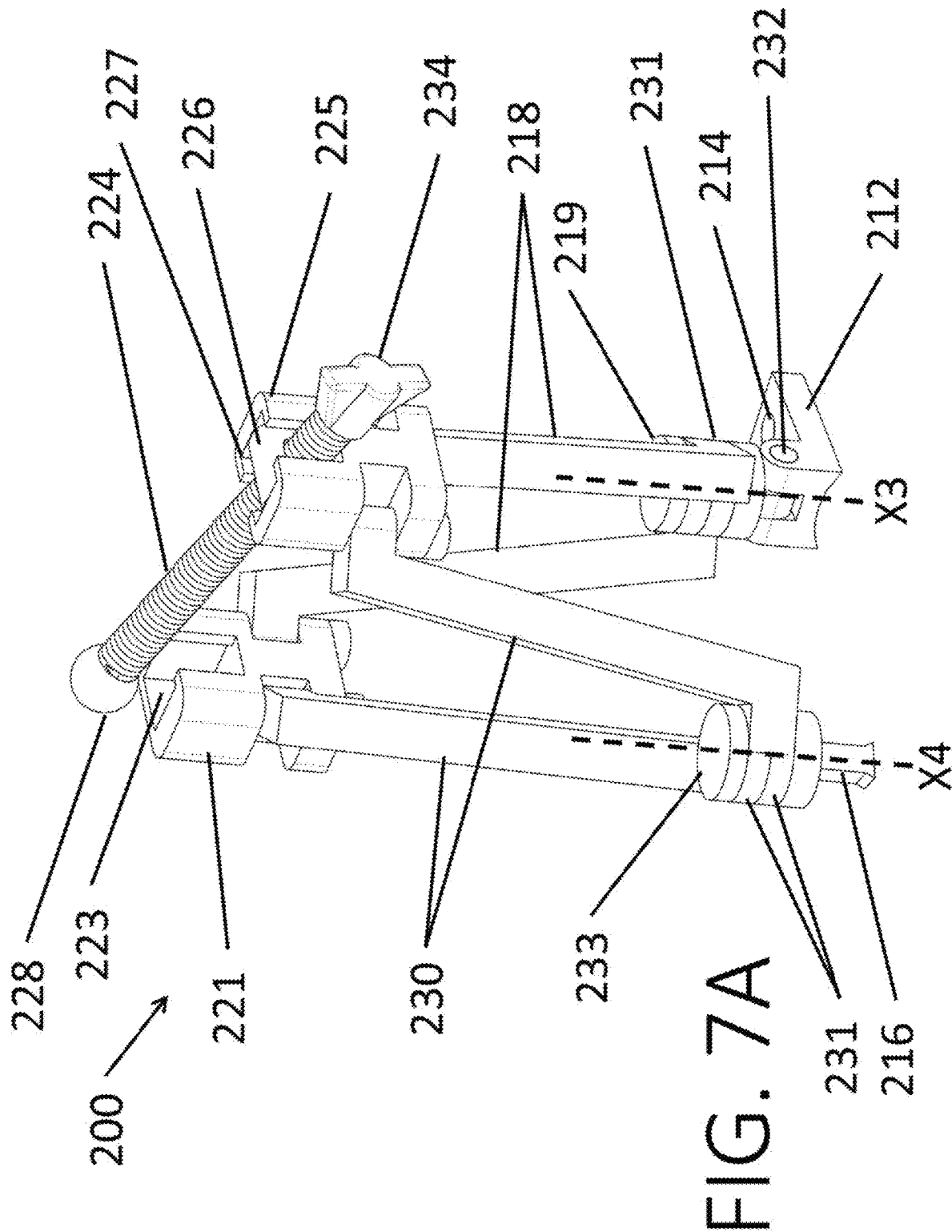
FIG. 7A is an oblique perspective view of an articulated tensioning device according to another aspect of the present disclosure in a partially assembled state.

FIGS. 7A-7C show an articulated tensioning device 200 including two feet in the form of a block 212 and a protrusion 216. Block 212 includes a fastener hole 214 for receiving a fastener to fix block 212 to a bone. Protrusion 216 is generally rectangular in cross-section and has a flared distal end defining two teeth extending away from one another. Like protrusions 16, 116, the shape of protrusion 216 facilitates dragging a bone plate, such as bone plate 36, by application of force to an edge of a fastener hole in the bone plate. In other arrangements, protrusion 216 could be any of the shapes of protrusions 16 and 116 illustrated in FIGS. 1A-6B or any of the alternatives thereto described above. Similarly, protrusions 16 and 116 could be made in the shape of protrusion 216 as illustrated in FIG. 7A.

Device 200 also includes two collars 221, 225, specifically, a socket collar 221 and a channel collar 225. Socket collar 221 defines a socket 223, whereas channel collar 225 defines a channel 227.

Block 212 and protrusion 216 are connected to collars 221, 225 by links 218, 230. Block side links 218 are each rotatably connected at one end to block 212 and at another end to one of the collars 221, 225. Specifically, one block side link 218 is rotatably connected to socket collar 221 and another block side link 218 is rotatably connected to channel collar 225. Similarly, protrusion side links 230 are each rotatably connected at one end to protrusion 216 and at another end to one of the collars 221, 225. One protrusion side link 230 is rotatably connected to socket collar 221 and another protrusion side link 230 is rotatably connected to channel collar 225.

Block side links 218 of the illustrated example each include a ring 231 that encircles a shank of a block pin 219 that is in turn rotatably connected to block 212 at block hinge 232. The shank, which is not visible in the figures, of block pin 219 defines a block pin axis X3 about which both block side links 218 are rotatable relative to block 212. Because block pin 219 is rotatably connected to block 212 by block hinge 219, block 212 itself is rotatable relative to block pin axis X3. The block side link 218 rotatably connected to socket collar 221 is rotatable relative to socket collar 221 about an axis parallel to, but not coaxial with, block pin axis X3. Similarly, the block side link 218 rotatably connected to channel collar 225 is rotatable relative to channel collar 225 about another axis parallel to, but not coaxial with, block pin axis X3. In other arrangements, block side links 218 may be rotatably connected to block 212 so as to be rotatable relative to block 212 about spaced apart, but parallel, axes.

Protrusion side links 230 of the illustrated example each include a ring 231 that encircles a shank of a protrusion pin 233 that is in turn connected to protrusion 216. The shank, which is not visible in the figures, of protrusion pin 233 defines a protrusion pin axis X4 about which both protrusion side links 233 are rotatable relative to protrusion 216. Protrusion pin axis X4 is parallel to block pin axis X3. The protrusion side link 230 rotatably connected to socket collar 221 is rotatable relative to socket collar 221 about an axis parallel to, but not coaxial with, protrusion pin axis X4. Similarly, the protrusion side link 230 rotatably connected to channel collar 225 is rotatable relative to channel collar 225 about another axis parallel to, but not coaxial with, protrusion pin axis X4. In other arrangements, protrusion side links 230 may be rotatably connected to protrusion 216 so as to be rotatable relative to protrusion 216 about spaced apart, but parallel, axes.

Links 218, 230 are all rigid, so each link prevents the axis about which it is rotatably connected to either collar 221, 225 from becoming parallel to either pin axis X3, X4. A distance between block 212 and protrusion 216 is therefore inversely related to a distance between collars 221, 225. Thus, the distance between block 212 and protrusion 216 can be reduced by forcing collars 221, 225 away from one another.

In the illustrated example, a bolt 224 has a threaded shank that extends through channel 227 of channel collar 225 and a head 228 that can be received in socket 223. Head 228 is freely rotatable in socket 223 when received therein, but prevented from escaping socket 223 by travelling toward channel collar 225 because head 228 has a diameter greater than a width of a lateral opening in socket 223. Head 228 is also prevented from escaping socket 223 by travelling away from channel collar 225 by a wall defining a side of socket 223 opposite from channel collar 225. When head 228 is received in socket 223 and a nut 226 is threaded onto the threaded shank of bolt 224 and received in channel 225, a bolt axis X5 that is defined along bolt 224 extends through both collars 221, 225 and perpendicular to pin axes X3, X4. When bolt 224 is positioned with head 228 received in socket 223 and with nut 226 received in channel 227 as shown in FIGS. 7B and 7C, nut 226 is constrained from rotating about or travelling along bolt axis X5 by openings at both ends of channel 227 being narrower than nut 226. Rotation of bolt 224 about bolt axis X5 when bolt 224 is positioned as shown in FIGS. 7B and 7C therefore causes head 228 and nut 226 to act on the walls defining the socket 223 and channel 227, respectively, to either force collars 221, 225 toward or away from one another, depending on the direction that bolt 224 is turned. Bolt 224 may be provided with a drivable or ergonomic feature, such as knob 234 at the proximal end of bolt 224 in the illustrated example, to facilitate turning bolt 224 about bolt axis X5. In other arrangements, channel collar 225 may have an integrally formed, internally threaded channel threadedly engaging bolt 224 instead of nut 226. Such other arrangements would otherwise function in the same manner as that described above with regard to the illustrated example.

Because the geometry of links 218, 230 creates an inverse relationship between the distance between block 212 and protrusion 216 and the distance between collars 221, 225 as described above, turning bolt 224 about bolt axis X5 to force collars 221, 225 together or apart will in turn force block 212 and protrusion apart or together, respectively. In the illustrated arrangement in particular, a reduction axis X6 intersects both pin axes X3, X4, bolt axis X5 is perpendicular to pin axes X3, X4, and reduction axis X6 is perpendicular to pin axes X3, X4 and bolt axis X5, all as shown in FIG. 7C. Block 212 and protrusion 216 therefore travel toward or away from one another on reduction axis X6 in response to rotation of bolt 224 about bolt axis X5. Device 200 may therefore be used to reduce a gap 40 between bone portions 41, 42 in a similar manner to what was illustrated and described above with regard to devices 10, 100 by fastening block 212 to a first bone portion 41 and hooking protrusion 216 into a fastener hole 37 of a bone plate 36 fastened to a second bone portion 42 so that reduction axis X6 extends across a gap 40 between bone portions 41, 42 and then turning bolt 224 about bolt axis X5 to force collars. 221, 225 apart.

Bolt 224, socket 223, and channels 227 together represent merely one example of a mechanism that can be used to drive collars 221, 225 apart. In other examples, collars 221, 225 could be bridged by, for example, a rack of a rack and pinion or ratcheting arrangement, a jack, or any other device capable of forcing collars 221, 225 apart and holding collars 221, 225 away from one another.

Figure 8A:
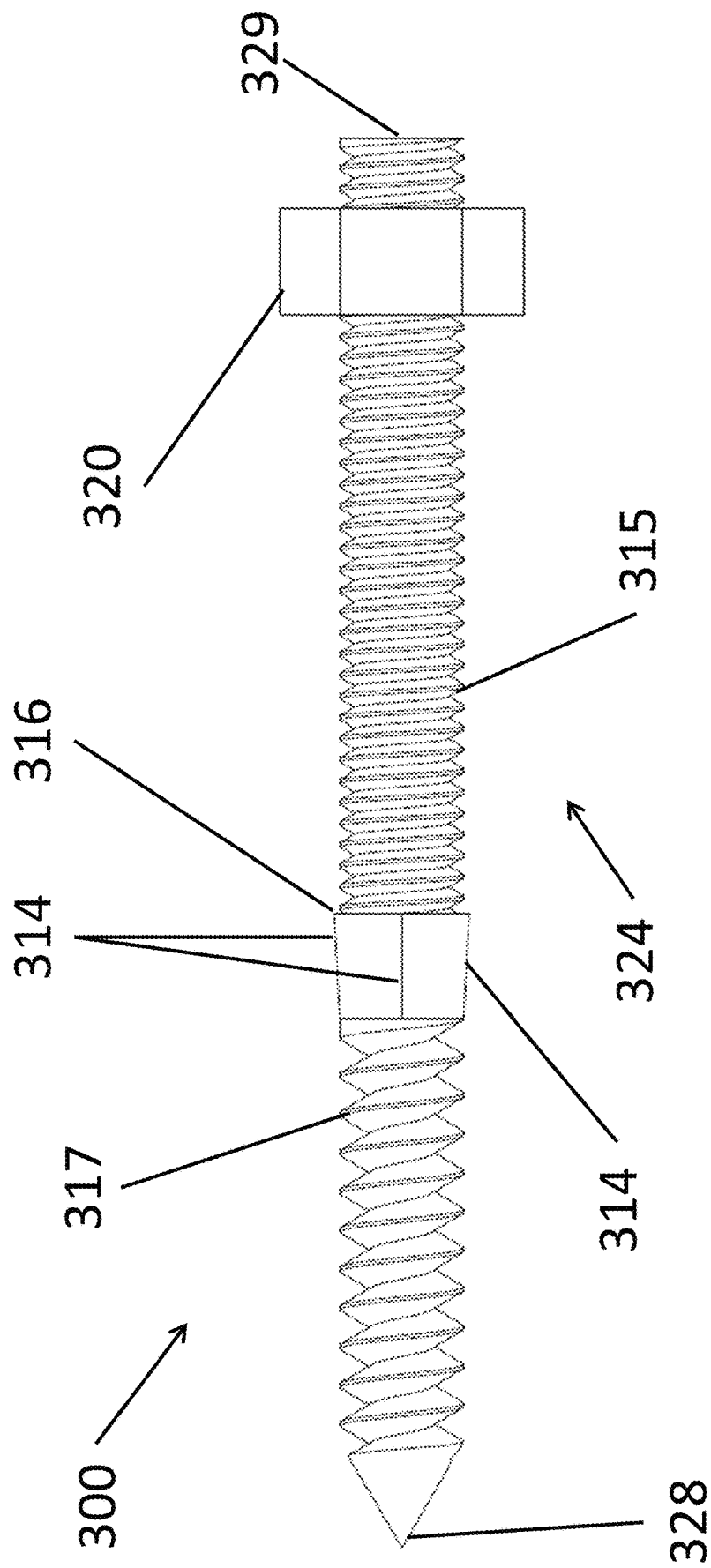
FIG. 8A is a side view of a reduction assembly according to another aspect of the present disclosure.
Figure 8B:
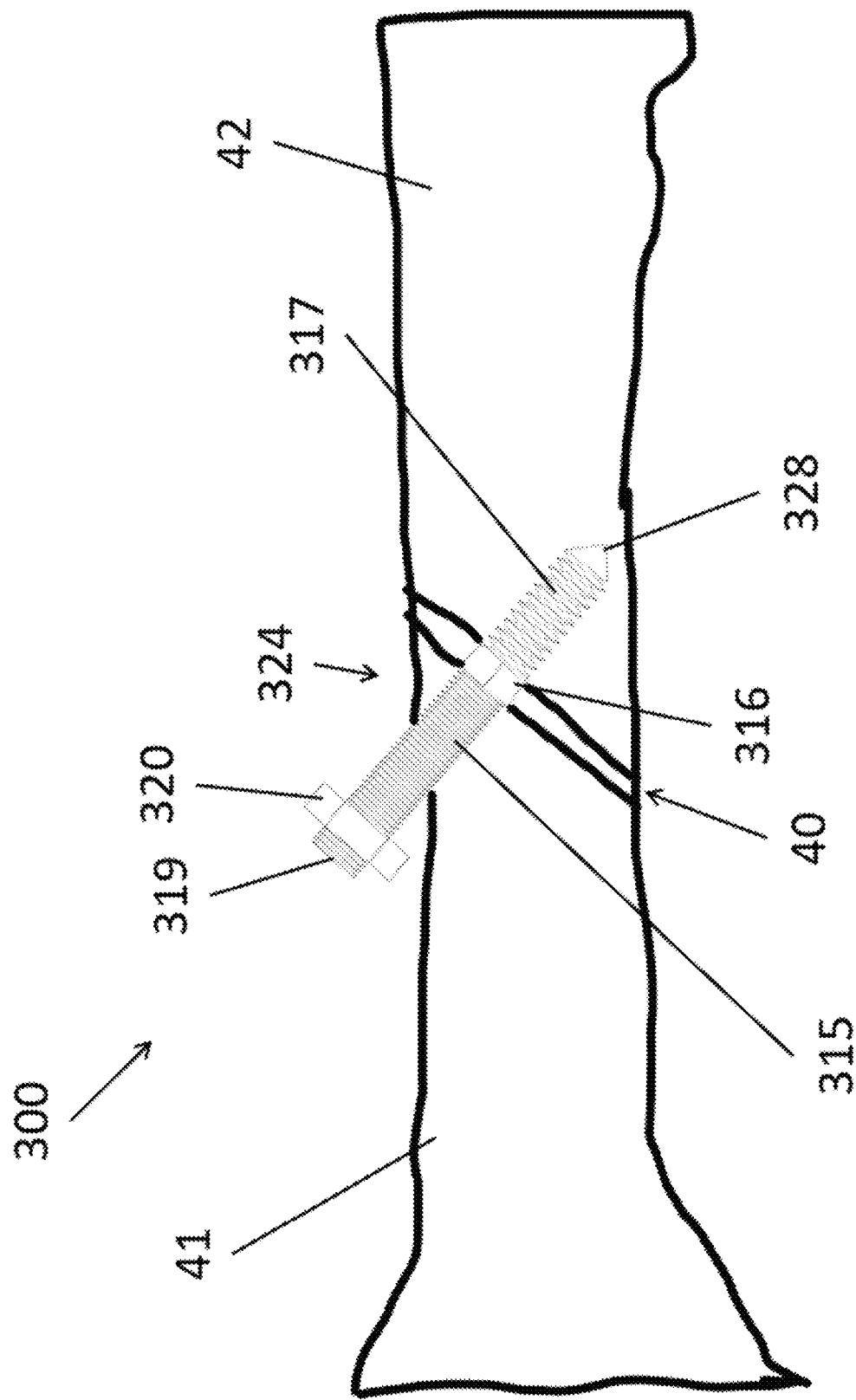
FIG. 8B is a cross-sectional view of a fractured bone in which the reduction assembly of FIG. 8A is embedded.

FIG. 8A illustrates a reduction assembly 300 comprising a screw 324 and a nut 320. Screw 324 includes an anchor 316 between proximal end 329 and distal end 328 of screw 324 so that a proximal portion 315 and a distal portion 317 of screw 324 are defined proximally and distally of anchor 316, respectively. In the illustrated arrangement, anchor 316 is near a proximal-distal midpoint of screw 324, but in various other arrangements anchor 316 may be nearer to either end 328, 329 of screw 324 than anchor 316 of the illustrated example. Though distal end 328 is depicted as pointed tip in the illustrated arrangement, distal end 328 may be flat or round in other examples, particularly if screw 324 is to be used in a pre-drilled pilot hole. Anchor 316 is a feature shaped to resist withdrawal of screw 324 proximally from an object in which anchor 316 is embedded. For example, if screw 324 is driven distally into a channel or hole narrow enough that anchor 316 digs into sides of the channel or hole as the screw 324 is driven, anchor 316 may engage those sides in a way that creates resistance to proximal movement of screw 324 within the channel or hole. Anchor 316 may be, in various examples, radially extending hooks that point proximally, a frustoconical segment of screw 324 with a greatest diameter at a proximal end thereof, an arrangement of inclined blades with distal-facing cutting edges 314 as shown in the illustrated example and similar to those commonly found at distal ends of bladed trocars, or any other feature or features more easily advanced distally into than withdrawn proximally from a narrow bore or solid object.

Nut 320 is threadedly engaged with threads on a proximal portion 315 of screw 324. Nut 320 also has a greater diameter than a minimum necessary diameter for a hole to be capable of accommodating distal advancement of any portions of screw 324 distal of the portion onto which nut 320 is threaded, including distal end 328, distal portion 317, anchor 316, and at least a distal part of proximal portion 315. A hole narrow enough that its sides would be engaged by anchor 316 when screw 324 is disposed therein may be too narrow to receive nut 320. Tension may be created on proximal portion 315 of screw 324 by advancing screw 324 distally through a narrow opening and, after anchor 316 becomes embedded, advancing nut 320 distally along proximal portion 315 until nut 320 abuts a surface in which the narrow opening is defined.

The above described potential for anchor 316 and nut 320 to create tension on the proximal portion 315 makes assembly 300 usable to reduce a gap 40 between bone portions 41, 42. In a process of using assembly 300 to reduce gap 40, screw 324 is advanced distally, meaning distal end 328 first, through an opening in a surface of first bone portion 41 that does not define an edge of gap 40. The opening may be preexisting, such as being a result of pre-drilling a hole into first bone portion 41, or the opening may be created by the distal advancement of screw 324 into first bone portion 41. In any case, the opening is too narrow to receive nut 320. Screw 324 continues to be advanced distally so that distal end 328 emerges from a surface of first bone portion 41 defining a first side of gap 40, travels across gap 40, and then advances into second bone portion 42 through a surface of second bone portion 42 that defines a second side of gap 40 opposite from the first side of gap 40. Screw 324 is driven far enough into second bone portion 42 that anchor 316 becomes embedded in second bone portion 42 and engages parts of second bone portion 42 adjacent to screw 324. While anchor 316 is embedded in second bone portion 42, nut 320 may be advanced as necessary to bear on the surface of first bone portion 41 through which distal end 328 first passed to enter first bone portion 41. Continued threaded advancement of nut 320 forces first bone portion 41 and second bone portion 42 together to reduce gap 40 and, in some examples, to press the surfaces of first bone portion 41 and second bone portion 42 that define opposite sides of gap 40 together.

Distal portion 317 of screw 324 may also be threaded as shown in the illustrated example. The threading of distal portion 317 may be optimized to facilitate distal advancement of screw 324 by rotation of screw 324 within bone. The threading of distal portion 317 may therefore differ from the threading of proximal portion 315. For example, the threading of distal portion 317 may be at a greater pitch than the threading of proximal portion 315 as shown in the illustrated arrangement. In some examples, the threading of distal portion 317 may be self-tapping or self-drilling so that screw 324 can be driven into bone prepared only with a narrow pilot hole or into bone not prepared with a hole for screw 324. In other examples, distal portion 317 may lack threads and screw 324 and impact force may be used to drive screw 324 linearly.

Figure 9A:
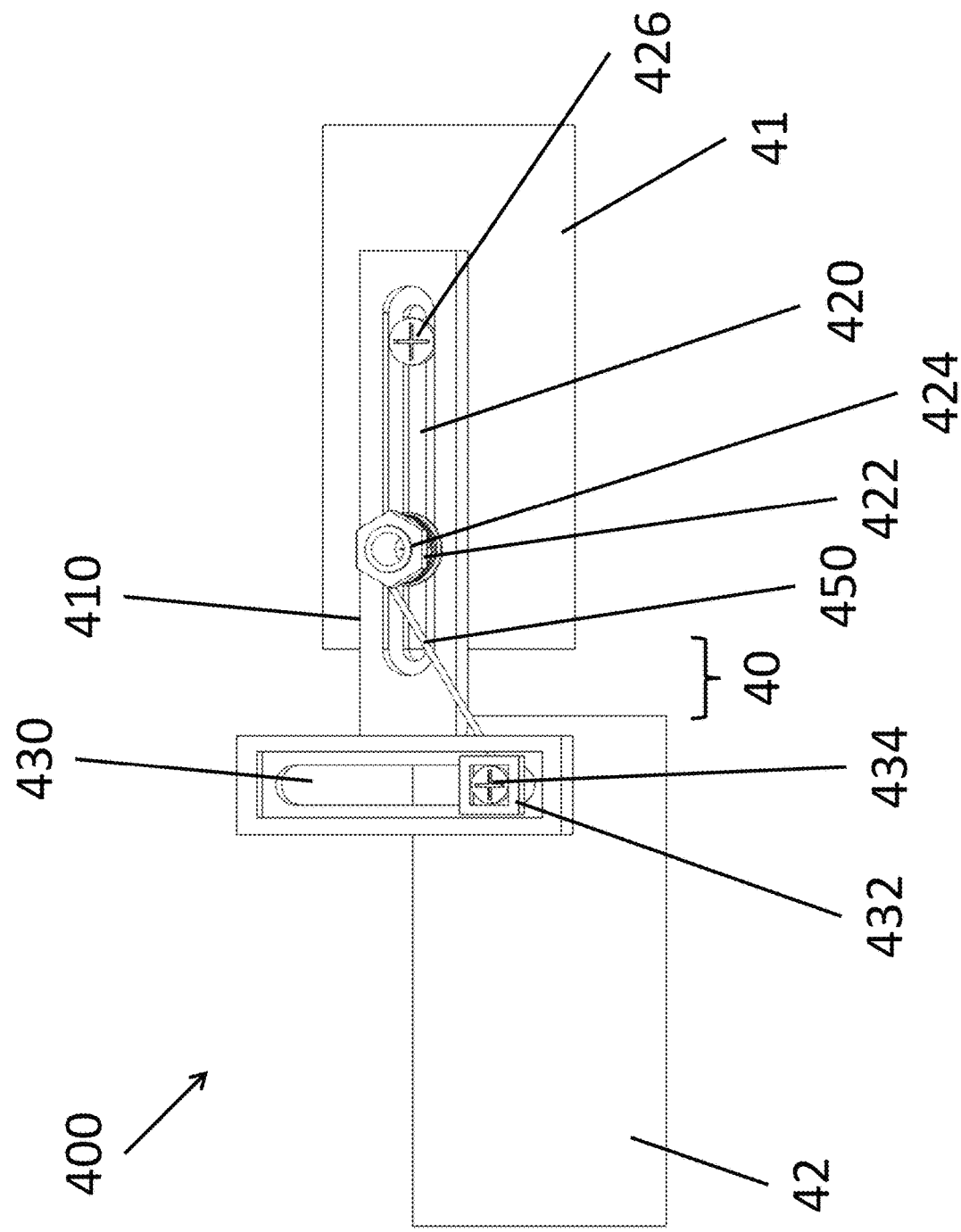
FIG. 9A is a perspective view of a reduction tool according to another aspect of the present disclosure fastened to two bone portions.
Figure 9B:
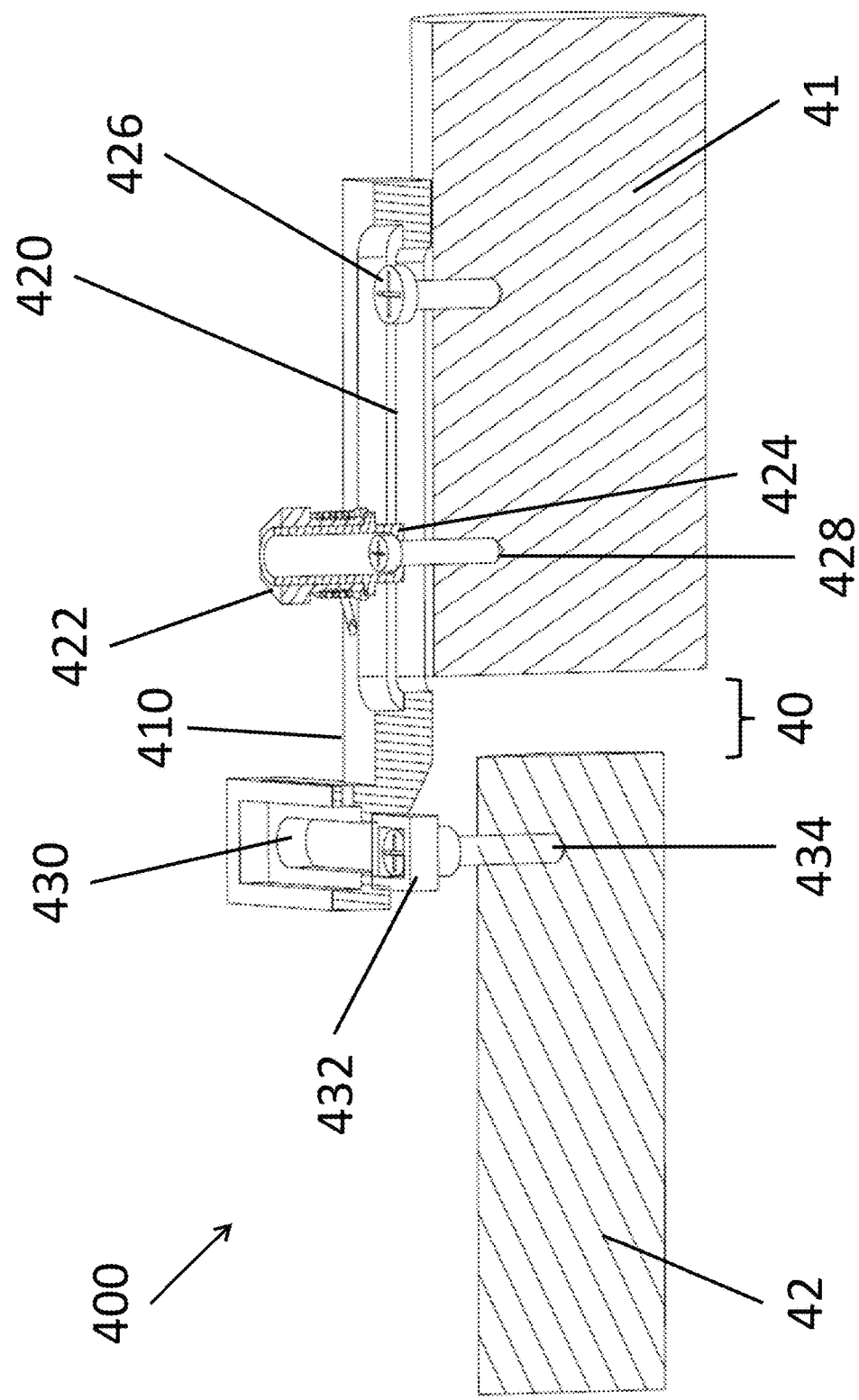
FIG. 9B is a cross-sectional view of the reduction tool and bone portions of FIG. 9A.

FIGS. 9A and 9B illustrate an assembly 400 for reducing a gap 40 between bone portions 41, 42. Assembly 400 includes a cross guide 410 that defines a first slot 420 and a second slot 430. First slot 420 and second slot 430 extend perpendicular to one another in the illustrated example, but in other examples, first slot 420 and second slot 430 may be neither parallel nor perpendicular to one another. Cross guides 410 having slots 420, 430 extending at various angles to one another may be suitable for different geometries of gap 40 and bone portions 41, 42. Similarly, though slots 420, 430 of the illustrated arrangements are linear, cross guides 410 according to other arrangements may have non-linear slots, and such non-linear slots may be useful for certain gap 40 and bone portion 41, 42 geometries.

Cross guide 410 is fastened to bone portions 41, 42 by screws 428, 434 extending through slots 420, 430 and into bone portions 41, 42. Specifically, at least one screw is disposed through first slot 420 and extends into first bone portion 41 and at least one screw is disposed through second slot 430 and extends into second bone portion 42, while no screw extends through first slot 420 into second bone portion 42 or through second slot 430 into first bone portion 41. First slot 420 extends along a length of first bone portion 41, so an optional third screw 426 may be disposed through first slot 420 to prevent assembly 410 from rotating relative to first bone portion 41. Screws 426, 428, 434 are all slidable within tracks 420, 430 so cross guide 410 can move relative to bone portions 41, 42 as screws 426, 428, 434 remain stationary relative to the bone portions into which they are driven. Screws 426, 428, 434 have heads greater in diameter than the width of slots 420, 430 in the illustrated example and therefore fasten cross guide 410 to the bone portions 420, 430.

A spool is provided by an axle 424 coupled to a proximal end of first screw 428 and a drum 422 rotatable about axle 424. In other arrangements, a spool could be provided by a drum that is rotatably coupled directly to a proximal end of a screw, without a distinct axle. A tether 450 is connected to drum 422 so that rotating drum 422 can wind tether 450 about drum 422. Tether 450 is also connected to screw 434, such as by attachment to a slider 432 coupled to a proximal end of screw 434 as shown in the illustrated example. Winding tether 450 around drum 422 therefore draws screws 428, 434 nearer to each other. Because screws 428, 434 are driven into first bone portion 41 and second bone portion 42, respectively, gap 40 can be reduced by turning drum 422 to wind tether 450 about drum 422. Drum 422 may be provided with a drivable feature, such as a hexagonal shaped portion at its proximal end as shown in the illustrated arrangement, a socket for engaging a screwdriver tip, or otherwise non-cylindrical portions located at the proximal end of drum 422 or anywhere else thereon.

Because first slot 420 and second slot 430 extend transverse to one another, winding tether 450 about drum 422 draws bone portions 41, 42 together along two axes. Specifically, the travel of screw 428 within first slot 420 toward second slot 430 reduces the width of gap 40 while the travel of screw 434 within second slot 430 toward alignment with the axis of first slot 420 reduces a lateral offset between bone portions 41, 42. Thus, assembly 400 can be used on misaligned bone portions 41, 42 to simultaneously bring bone portions 41, 42 into alignment and reduce gap 40 between bone portions 41, 42. The exact alignment between bone portions 41, 42 and the size of gap 40 that will result when tether 450 is wound to reach a minimum possible distance between screws 428, 434 depends on the locations of screws 428, 434 in bone portions 41, 42. The placement of screws 428, 434 may therefore be determined on a case-by-case basis to account for variations in the geometry of bones 41, 42 and gap 40.

Figure 10:
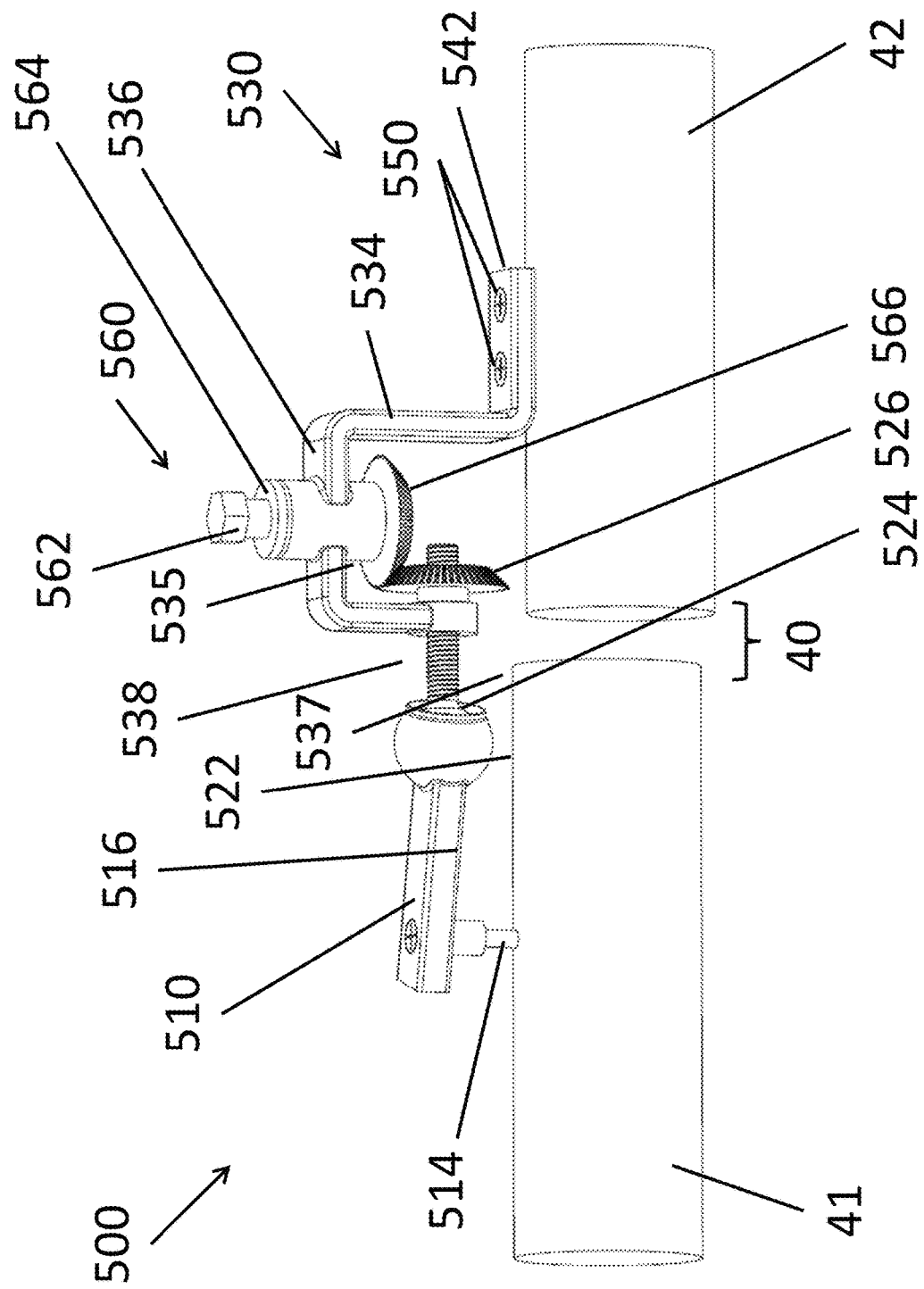
FIG. 10 is a perspective view of a reduction assembly according to another aspect of the present disclosure fastened to two bone portions.

FIG. 10 illustrates a reduction assembly 500 that includes a link 510 connected to a frame 530. Link 510 is connected to a bolt 522 that extends through an aperture 537 in frame 530. A gear nut 526 having a greater diameter than aperture 537 is threaded onto a portion of bolt 522 on an opposite side of aperture 537 from link 510. A driver 560 rotatably disposed through another aperture 535 of frame 530 includes a gear wheel 566 engaged with gear nut 526. Driver 560 may therefore be rotated to threadedly advance gear nut 526 along bolt 522 toward link 510. Because gear nut 526 has a greater diameter than aperture 537, advancing gear nut 526 along bolt 522 toward link 510 draws bolt 522 through aperture 537 and draws link 510 toward aperture 537. Link 510 may be fastened to first bone portion 41 and frame 530 may be fastened to second bone portion 42 to enable reduction of gap 40 by rotation driver 560 to advance gear nut 526 along bolt 522 toward link 510.

Link 510 may be fastened to first bone 41 by a screw 514. Optionally, link 510 may be pivotable about screw's 514 central axis. Bolt 522 may optionally be connected to link 510 in a manner that permits rotation of bolt 522 relative to link 510 about an axis parallel to screw's 514 central axis. Where link 510 is rotatable about screw 514 about an axis parallel to an axis about which bolt 522 is rotatable relative to link 510, the above described use of gear nut 526 to draw bolt 522 through aperture 537 may laterally align bone portions 41, 42 in addition to reducing gap 40. In the illustrated example, a rotatable connection between link 510 and bolt 522 is provided by a spherical socket 516 of link 510 in which a spherical head 524 of bolt 522 is received to create a ball joint. In other arrangements, a rotatable connection between link 510 and bolt 522 may instead be provided by a ball joint created by a socket defined in bolt 522 and a spherical end of link 510 or by a hinge that only permits rotation of bolt 522 relative to link 510 about one axis.

Frame 560 of the illustrated example includes an arch defined by a support 534 rising from a base 542 configured to lie on a surface of a bone portion, a peak 536 providing a highest portion of the arch and extending transverse to support 534, and a hanging portion 538 that extends from a location on peak 538 spaced from the location where arch 534 meets peak 536. Hanging portion 538 extends from peak 536 in a direction generally opposite from the direction that support 534 extends from base 542. Aperture 537 is defined through hanging portion 538 and aperture 535 is defined through peak 536. Because apertures 535, 537 closely fit driver 560 and bolt 522, respectively, and hanging portion 538 extends transverse to peak 564, bolt 522 and driver 560 extend along non-parallel axes. In the illustrated example specifically, hanging portion 538 and peak 536 extend on perpendicular planes and bolt 522 and driver 560 extend along perpendicular axes. Gear wheel 566 and gear nut 526 are each bevel gears and can therefore transfer torque on driver 560 about driver's 560 central axis to torque on gear nut 526 about bolt 522. In other arrangements hanging portion 538 and peak 536 may extend on planes that are neither not perpendicular to each other and driver 560 and bolt 522 may extend on axes that are neither parallel nor perpendicular to each other. In still further arrangements, apertures 535, 537 may be located elsewhere on frame 530 and gear nut 526 and gear wheel 566 may be other types of gear. For example, aperture 535 could be relocated to support 534 so that driver 560 extends parallel to bolt 522 and gear wheel 566 and gear nut 526 may be non-beveled gears.

Base 542 extends from support 534 in a direction transverse to support 534 so that support 534 may extend away from a surface of a bone on which base 542 lies. Base 542 may be fastened to a bone by one or more screws 550 or other fasteners. Base 542 may be provided with any number of holes for accepting fasteners. For example, base 542 of some examples may include only a single fastener hole, though the use of multiple fasteners such as the two screws 550 to fasten base 542 to the bone as shown in the illustrated example prevents rotation of frame 530 relative to the bone.

Driver 560 of the illustrated example includes features to facilitate rotation of driver 560 within aperture 535 while otherwise presenting movement of driver 560 relative to frame 530. To facilitate transmission of torque to driver 560, a proximal end of driver 560 includes a non-cylindrical drive head 562. Drive head 562 is hexagonal in the illustrated example, but could be any polygonal or non-cylindrical shape or could include a socket to receive an end of a driving tool in other arrangements. Driver 564 includes a ring 564 of greater diameter than aperture 535 spaced from gear wheel 566 by a distance equal, or at least approximately equal, to the length of aperture 535. Gear wheel 566 also has a greater diameter than aperture 535, so the portion of frame 530 defining aperture 535 is trapped between ring 564 and gear wheel 566 and translation of driver 560 within aperture 535 is limited or prevented. In other arrangements, ring 564 could be omitted to allow driver 560 to move relative to frame 530, or another ring could be provided between gear wheel 566 and aperture 535.

Figure 11A:
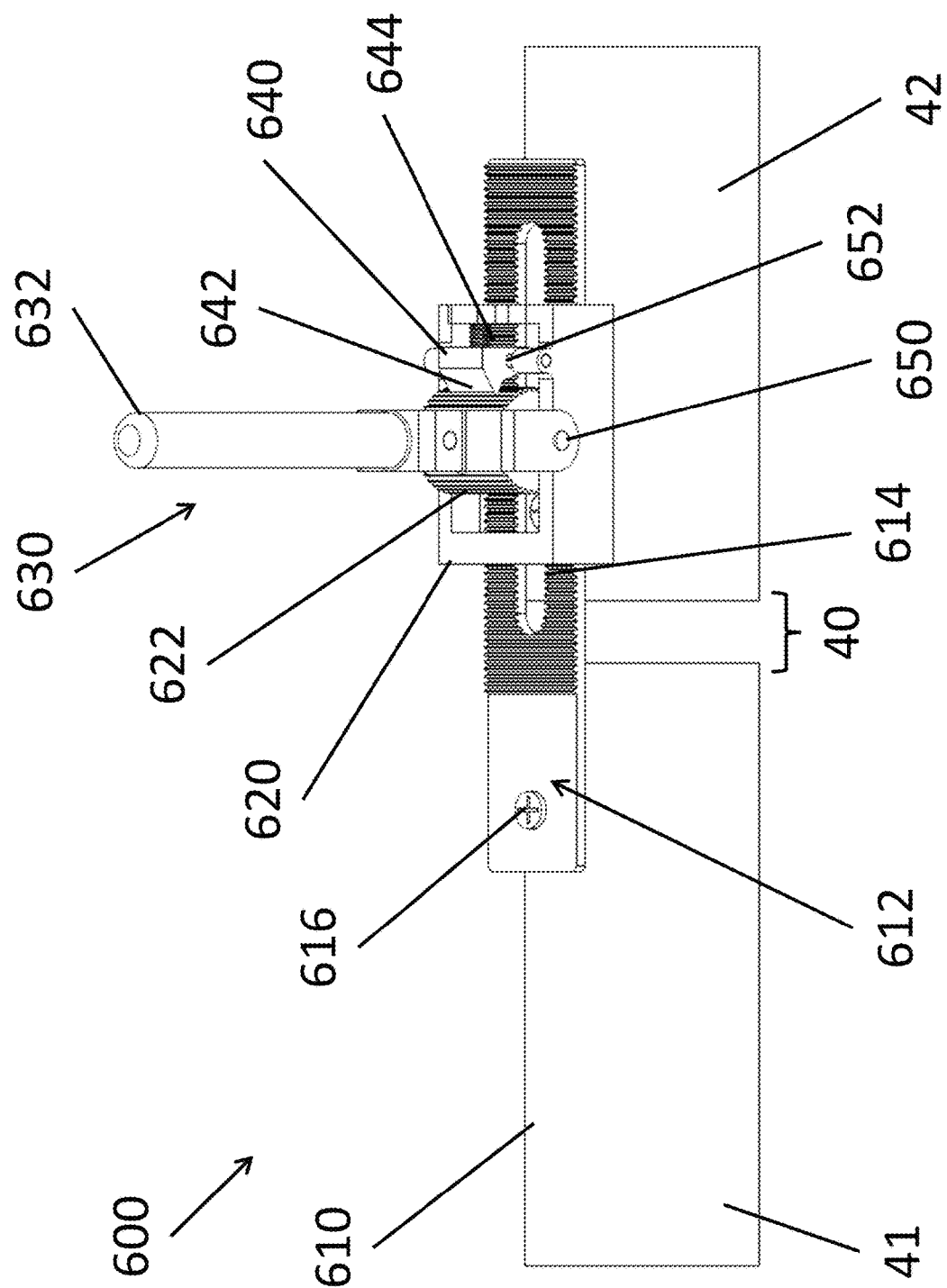
FIG. 11A is a perspective view of a reduction assembly according to another aspect of the present disclosure fastened to two bone portions.
Figure 11B:
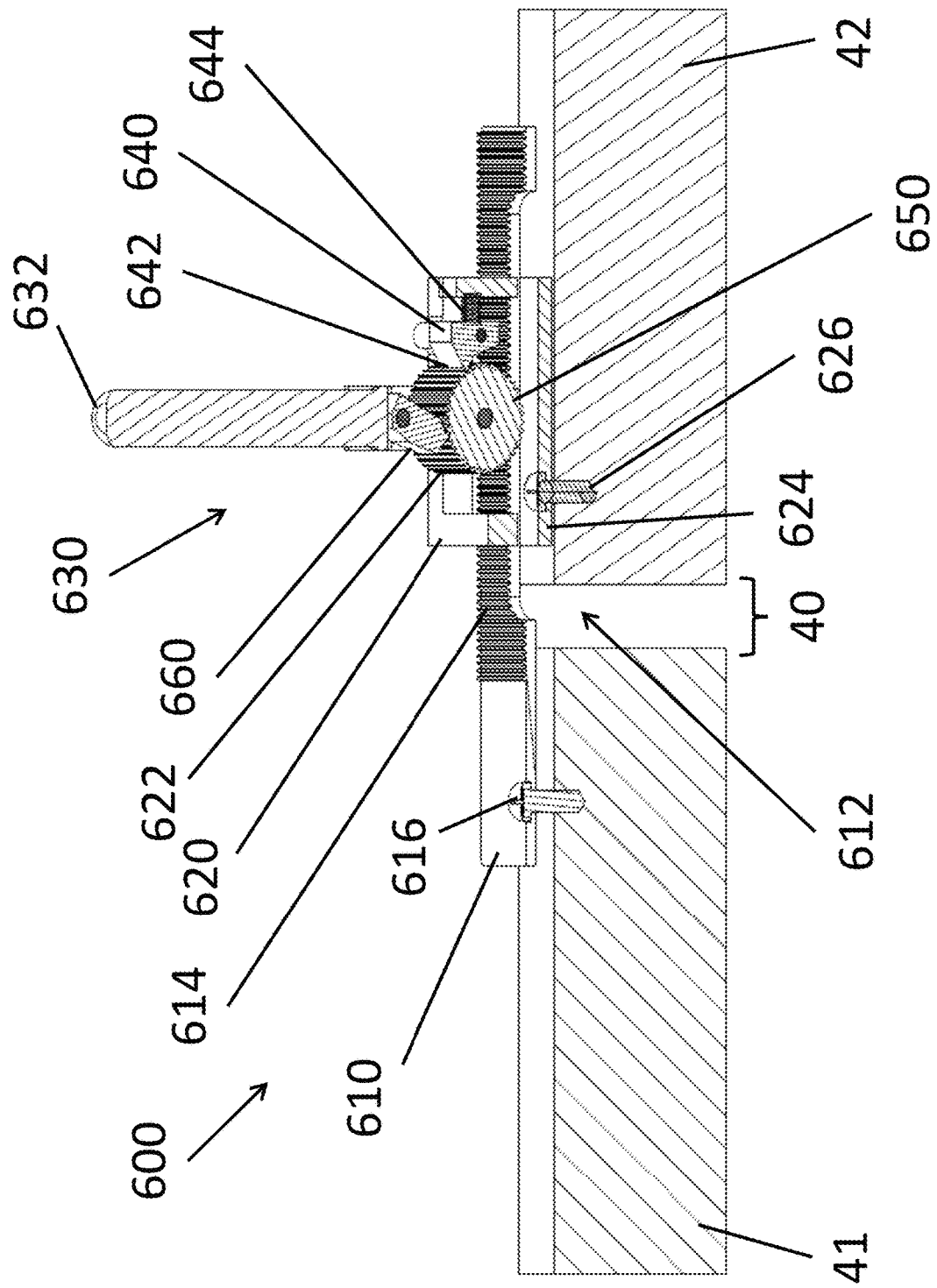
FIG. 11B is a cross-sectional view of the reduction assembly and bone portions of FIG. 11A.

FIGS. 11A and 11B illustrate a reduction assembly 600 including a plate 610, a frame 620, and a pinion 622. Plate 610 includes a series of teeth defining a rack 612 with which pinion 622 is engaged. Pinion 622 is rotatably connected to frame 620 so that rotating pinion 622 relative to frame 620 to cause pinion 622 to travel along rack 612 also draws frame 620 along plate 610. Thus, when plate 610 is fastened to first bone portion 41 and frame 620 is fastened to second bone portion 42, pinion 622 may be advanced along rack 612 to reduce gap 40.

To facilitate driving pinion 622 along rack 612, a lever 630 may be pivotably connected to frame 620 and engaged with pinion 622 to transmit force on lever 630 to torque on pinion 622. Lever 630 and pinion 622 may be rotatable about a common axis and, optionally, a common axle 650 as shown in the illustrated arrangement. In the illustrated example, lever 630 includes a pawl 660 having an edge capable of engaging teeth of pinion 622. Pawl 660 is rotatable relative to a handle 632 of lever 630 so that pawl 660 can pivot out of engagement with pinion's 622 teeth when lever 630 is turned in one direction, but can remain in engagement with pinion's 622 teeth when lever 630 is turned in another direction. Specifically, pawl 660 can only transmit torque to pinion 622 in a direction that advances pinion 622 toward a feature of plate 610 connectable to bone, such as a fastener hole in which screw 616 is received in the illustrated example. Pawl 660 therefore interacts with pinion 622 in a ratcheting manner. Thus, when plate 610 is fastened to first bone portion 41 and frame 620 is fastened to second bone portion 620, gap 40 may be reduced by alternately turning lever 630 counterclockwise from the perspective of FIGS. 11A and 11B so that pawl 660 causes pinion 622 to turn counterclockwise and advance along pinion 612 and turning lever 630 clockwise so that pawl 660 drags along pinion's 622 teeth without causing pinion 622 to rotate.

Optionally, another pawl 640 may be connected to frame 620 to prevent pinion 622 from rotating in a direction opposite the direction that pawl 660 may transmit torque to pinion 622. Pawl 642 may be pivotably connected to frame 620 but biased into engagement with pinion 622 by a spring 644 as shown. In other arrangements, pawl 640 may be non-rotatably connected to frame 620 and constructed of a relatively flexible material, such as rubber, plastic, or a flexible metal or metal alloy, and shaped so that pawl 640 may elastically deform to permit pinion's 622 teeth to pass pawl 640 in only one direction.

Frame 620 of the illustrated example includes a panel 624 defining at least one fastener hole to facilitate fastening frame 620 to bone. In the illustrated arrangement specifically, a screw 626 extends through panel 624 to fasten frame 620 to second bone portion 42. A slot 614 is defined through plate 614 to provide easy access to panel 624 and screw 626. However, in other arrangements, slot 614 may be omitted, and in still further arrangements panel 624 may be located elsewhere or omitted and other features may be provided to facilitate fastening frame 620 to bone.

Any of the devices described in the present disclosure can be made of any sufficiently strong, durable, and biocompatible materials. Examples of suitable metals or metal alloys suitable for this purpose include stainless steel, titanium, nitinol, and any other biocompatible metals or metal alloys. Examples of suitable polymers include high-density polyethylene ("HDP"), polymethylmethacrylate ("PMMA"), polyetheretherketone ("PEEK"), or any other rigid and biocompatible polymer. In further examples, some or all components of any of the foregoing devices may be constructed of ceramic.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An articulated tensioning device, comprising:
   a first foot and a second foot, wherein either the first foot or the second foot includes a projection configured to engage a fastener hole of a bone plate and the other of the first foot and the second foot includes a hole therethrough for receiving a fastener;
   a slider translatable relative to the first foot;
   a bridge link pivotably connected to the slider at a first point and pivotably connected to the second foot at a second point; and
   a fulcrum link pivotably connected to the second foot and a third point on the bridge link that is between the first point and the second point.

2. The tensioning device of claim 1, wherein the bridge link is a first bridge link and comprising a second bridge link pivotably connected to the slider at a fourth point and pivotably connected to the second foot at a fifth point.

3. The tensioning device of claim 2, wherein the fulcrum link is a first fulcrum link and further comprising a second fulcrum link pivotably connected to the second foot and a sixth point on the bridge link that is between the fourth point and the fifth point.

4. The tensioning device of claim 1, comprising a guide that constrains translation of the slider to an axis defined relative to the guide.

5. The tensioning device of claim 4, wherein the guide is nontranslatable relative to the first foot.

6. The tensioning device of claim 5, wherein the guide axis is immovable relative to the first foot.

7. The tensioning device of claim 4, wherein the guide comprises a shaft extending through the slider, wherein the slider is translatable along the shaft.

8. The tensioning device of claim 7, wherein the shaft is externally threaded and the guide is internally threaded.

9. The tensioning device of claim 4, comprising a post extending from the second foot, a collar slidable along the post, and an arm pivotably connected to the collar and to a fixed point on the guide.

10. The tensioning device of claim 9, wherein the post is non-rotatable relative to the second foot.

11. The tensioning device of claim 10, wherein the arm is a first arm, and comprising a second arm extending from the collar.

12. The tensioning device of claim 4, wherein the guide comprises a track link that defines an elongate track extending parallel to the guide axis and the slider includes a stud received in the track.

13. An articulated tensioning device, the device comprising:
   a first foot and a second foot, wherein either the first foot or the second foot includes a projection configured to engage a fastener hole of a bone plate and the other of the first foot and the second foot includes a hole therethrough for receiving a fastener;
   a first collar and a second collar;
   a first link connected to the first foot, rotatable relative to the first foot about a first axis, connected to the first collar, and rotatable relative to the first collar about a second axis,
   a second link connected to the first foot, rotatable relative to the first foot about a third axis, connected to the second collar, and rotatable relative to the second collar about a fourth axis;
   a third link connected to the second foot, rotatable relative to the second foot about a fifth axis, connected to the first collar, and rotatable relative to the first collar about a sixth axis; and
   a fourth link connected to the second foot, rotatable relative to the second foot about a seventh axis, connected to the second collar, and rotatable relative to the second collar about an eighth axis;
   wherein the first, second, third, fourth, fifth, sixth, seventh, and eighth axes are parallel to one another and none of the first, third, fifth, or seventh axes are coaxial with any of the second, fourth, sixth, or eighth axes.

14. The tensioning device of claim 13, comprising a threaded shank extending through the first collar and into the second collar.

15. The tensioning device of claim 14, wherein the first collar includes an internally threaded portion.

16. The tensioning device of claim 14, comprising a nut threaded onto the threaded shank and received in the first collar.

17. The tensioning device of claim 14, comprising a bolt including the threaded shank and a head, the head being rotatably received in a socket defined by the second collar.

18. The tensioning device of claim 17, wherein the head is at least partially spherical.

19. The tensioning device of claim 13, further comprising a shank rotatable about a ninth axis perpendicular to the first, second, third, fourth, fifth, sixth, seventh, and eighth axes.

20. The tensioning device of claim 13, wherein the first axis is coaxial with the third axis and the fifth axis is coaxial with the seventh axis.

* * * * *